US012000830B2

(12) United States Patent
Lipkin et al.

(10) Patent No.: US 12,000,830 B2
(45) Date of Patent: Jun. 4, 2024

(54) SEROLOGICAL ASSAY FOR THE DETECTION OF ZIKA VIRUS-SPECIFIC ANTIBODIES UTILIZING OVERLAPPING PEPTIDES COMPRISING AN NS2B EPITOPE

(71) Applicant: THE TRUSTEES OF COLUMBIA UNIVERSITY IN THE CITY OF NEW YORK, New York, NY (US)

(72) Inventors: Walter Ian Lipkin, New York, NY (US); Nischay Mishra, New York, NY (US); Thomas Briese, White Plains, NY (US); Adrian Caciula, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 706 days.

(21) Appl. No.: 16/466,161

(22) PCT Filed: Dec. 1, 2017

(86) PCT No.: PCT/US2017/064167

§ 371 (c)(1),
(2) Date: Jun. 3, 2019

(87) PCT Pub. No.: WO2018/102659

PCT Pub. Date: Jun. 7, 2018

(65) Prior Publication Data

US 2019/0359694 A1 Nov. 28, 2019

Related U.S. Application Data

(60) Provisional application No. 62/428,845, filed on Dec. 1, 2016.

(51) Int. Cl.

| | |
|---|---|
| ***G01N 33/569*** | (2006.01) |
| ***A61K 35/76*** | (2015.01) |
| ***C07K 7/00*** | (2006.01) |
| ***C07K 16/06*** | (2006.01) |
| ***C07K 16/10*** | (2006.01) |

(52) U.S. Cl.

CPC ....... *G01N 33/56983* (2013.01); *A61K 35/76* (2013.01); *C07K 7/00* (2013.01); *C07K 16/06* (2013.01); *C07K 16/1081* (2013.01); *C07K 2317/21* (2013.01); *C07K 2317/34* (2013.01); *G01N 2333/185* (2013.01)

(58) Field of Classification Search

CPC ....... G01N 2333/185; G01N 33/56983; C07K 7/00; C12N 2770/24122

See application file for complete search history.

(56) References Cited

U.S. PATENT DOCUMENTS

| | | | |
|---|---|---|---|
| 7,785,799 B2 | 8/2010 | Barrett et al. | |
| 2021/0205434 A1* | 7/2021 | Petsch | A61K 39/12 |

FOREIGN PATENT DOCUMENTS

| | | |
|---|---|---|
| WO | WO 2017/031353 | 2/2017 |
| WO | WO 2017/140905 | 8/2017 |

OTHER PUBLICATIONS

Abbink, P., et al., 2016, Protective efficacy of multiple vaccine platforms against Zika virus challenge in Rhesus monkeys, Science 353(6304):1129-1132.*

Phoo, W. W., et al., Nov. 2016, Structure of the NS2B-NS3 protease from Zika virus after self-cleavage, Nat. Comm. 7(13410):1-8.*

Stephenson, K. E., et al., 2015, Quantification of the epitope diversity of HIV-1-specific binding antibodies by peptide microarrays for global HIV-1 vaccine development, J. Immunol. Methods 416:105-123, available online Nov. 15, 2014).*

Abbink, P., et al., Sep. 2016a, Protective efficacy of multiple vaccine platforms against Zika virus challenge in rhesus monkeys, Science 353(6304):1129-1133.*

Abbink, P., et al., Sep. 2016b, Protective efficacy of multiple vaccine platforms against Zika virus challenge in rhesus monkeys, Science 353(6304):1129-1133, supplementary materials, pp. 1-20.*

(Abbink, Petal.) Protective Efficacy of Multiple Vaccine Platforms Against Zika Virus Challenge in Rhesus Monkeys. Science. Sep. 9, 2016, vol. 353, No. 6304, pp. 1129-1132; abstract; p. 2, 1st paragraph; p. 2, 3rd paragraph; p. 3, 4th paragraph; p. 4, 1st paragraph; supplemental p. 2, 2nd paragraph; supplemental p. 3, 3rd paragraph; supplemental p. 3, 4th paragraph; supplemental p. 4, 1st paragraph; DOI: 1 0,1126/science.aah6157.

(Phoo, WW et al.) Structure of the NS2B-NS3 protease from Zika virus after self-cleavage. Nature. Nov. 15, 2016, vol. 7, No. 13410, pp. 1-8; p. 2, 1st col. 1st paragraph; p. 2, 1st col. 2nd paragraph; p. 3, 1st col. 1st paragraph; Figure 1; supplementary figure 1; DOI: 10.1038/ncomms13410.

(Dar, H et al.) Prediction of promiscuous T-cell epitopes in the Zika virus polyprotein: An in silica approach. Asian Pacific Journal of Tropical Medicine. Jul. 26, 2016, vol. 9, No. 9; pp. 844-850; DOI: 10.1016/j.apjtm.2016.07.004.

(Xu, X et al.) Identifying Candidate Targets of Immune Responses in Zika Virus Based on Homology to Epitopes in Other Flavivirus Species. PLoS Currents. Nov. 15, 2016, Edition 1; DOI: 1 0.1371/currents.outbreaks.9aa2e1fb61b0f632f58a098773008c4b.

(Mohr, EL et al.) Differentiating Zika and Dengue virus infections with a linear peptide array. American Society of Tropical Medicine & Hygiene. Poster Presentation [online]. Nov. 5, 2017 [Retrieved on Feb. 12, 2018]. Retrieved from the Internet: <URL: https://zika .lab key.com/wiki/OConnor/download.view?entityId=3a020e26-ac 7 c-1 035-9030-0dc06b4aa65a&name=Emma Mohr_ASTMH_2017 .pdf>; entire document.

(Continued)

*Primary Examiner* — Jeffrey S Parkin

(74) *Attorney, Agent, or Firm* — Amster, Rothstein & Ebenstein LLP

(57) ABSTRACT

The current invention provides compositions, methods, and kits for detecting the exposure to and infection by certain viruses. Specifically, the current invention allows for the rapid differential serological detection of exposure to, and infection by viruses. In particular, the current invention allows for the rapid serological detection of exposure to, and infection by Zika virus (ZIKV).

20 Claims, 3 Drawing Sheets

Specification includes a Sequence Listing.

(56) References Cited

OTHER PUBLICATIONS (Steinhagen, Ketal.) Serodiagnosis of Zika virus (ZIKV) infections by a novel NS1-based ELISA devoid of cross-reactivity with dengue virus antibodies: a multicohort study of assay performance, 2015 to 2016. Eurosurveillance. Dec. 15, 2016, vol. 21, No. 50; pp. 1-16; DOI: 10.2807/1560-7917.ES.2016.21.50.30426.

Anderson et al., "Development and evaluation of a Luminex multiplex serology assay to detect antibodies to bovine herpes virus 1, parainfluenza 3 virus, bovine viral diarrhea virus, and bovine respiratory syncytial virus, with comparison to existing ELISA detection methods", J. Immunol. Methods Jan. 28, 2011;366:79-88.

Broutet et al., "Zika Virus as a Cause of Neurologic Disorders", N. Engl. J. Med. Apr. 21, 2016;374(16):1506-9.

Buus et al., "High-resolution Mapping of Linear Antibody Epitopes Using Ultrahigh-density Peptide Microarrays", Mol. Cell Proteomics Sep. 13, 2012;11:1790-800.

Rasmussen et al., "Zika Virus and Birth Defects—Reviewing the Evidence for Causality", N. Engl. J. Med. May 19, 2016;374(20):1981-7.

Robinson et al., "Autoantigen microarrays for multiplex characterization of autoantibody responses", Nat. Med. Mar. 2002;8:295-301.

Vigil et al., "Defining the humoral immune response to infectious agents using high-density protein microarrays", Future Microbiol. Feb. 2010;5:241-51. PMC2841399.

* cited by examiner

SEROLOGICAL ASSAY FOR THE DETECTION OF ZIKA VIRUS-SPECIFIC ANTIBODIES UTILIZING OVERLAPPING PEPTIDES COMPRISING AN NS2B EPITOPE

CROSS-REFERENCE TO RELATED PATENT APPLICATIONS

This application is a U.S. National Phase Application under 35 U.S.C. § 371 of International Patent Application No. PCT/US2017/064167, filed Dec. 1, 2017, which claims the priority of U.S. Provisional Patent Application 62/428,845, filed Dec. 1, 2016, all of which are incorporated by reference, as if expressly set forth in their respective entireties herein.

STATEMENT OF GOVERNMENT SUPPORT

This invention was made with government support under AI109761 awarded by the National Institutes of Health. The government has certain rights in this invention.

FIELD OF THE INVENTION

This invention relates to the field of detection of exposure to viruses, using high throughput serology, in particular the detection of exposure to Zika virus (ZIKV).

BACKGROUND OF THE INVENTION

Zika virus (ZIKV) is an emerging mosquito-borne virus that affects several major continents including Africa, Asia, and the Americas, and has been deemed a global emergency by the World Health Organization (WHO). ZIKV infection carries high risk for pregnant women as it has been causally linked to severe fetal brain anomalies such as microcephaly, intracranial calcifications, and fetal brain disruption sequence as well as ocular anomalies (Rasmussen et al. 2016). Furthermore, ZIKV infection likely triggers an increased risk for Guillain-Barré syndrome (Broutet et al. 2016).

In urban and suburban environments, ZIKV is transmitted in a human-mosquito-human transmission cycle. In addition to mosquito transmission, evidence indicates that ZIKV can be transmitted from the mother to the fetus during pregnancy. Additionally, sexual transmission to partners has also been reported. Finally, although the transmission of ZIKV through a blood transfusion has not been reported, it is likely to occur, given the transmission of other, related flaviviruses, through this route.

Zika virus is a flavivirus, closely related to dengue virus (DENV). ZIKV diagnosis is often based on clinical symptoms and epidemiological links Zika virus and dengue virus, as well as other viruses, i.e., West Nile virus (flavivirus) and chikungunya virus (alphavirus) infections, also present with similar clinical symptoms causing difficulty in differential diagnosis. Molecular assays for detection of Zika virus gene products are useful in diagnosis of active infection but cannot provide insight into historical infection that may influence the development of offspring in utero after the acute infection has cleared. Cross-reactivity between ZIKV and DENV in current serological assays confounds clinical diagnosis and efforts to investigate the prevalence of infection and the linkage to disease. Indeed, the Centers for Disease Control and Prevention recommends that all samples found seropositive in the current ZIKV ELISA be validated in plaque reduction neutralization tests (PRNT).

PRNTs are expensive, labor intensive and require live virus, thus, PRNTs are difficult to implement in clinical microbiology laboratories.

Additionally, vaccines for ZIKV are at the forefront of research. As these vaccines are developed, there is a need for rapid reliable assays for testing the efficacy of such vaccines.

Thus, there is a need for a sensitive, specific, and inexpensive high throughput serological assay for the diagnosis of ZIKV exposure.

SUMMARY OF THE INVENTION

The current invention provides compositions, methods, devices, and kits for detecting the exposure to, and infection by, certain viruses. Specifically, the current invention allows for the rapid differential serological detection of exposure to, and infection by viruses. In particular, the current invention allows for the rapid serological detection of exposure to, and infection by Zika virus (ZIKV).

The compositions, methods, devices, and kits for detection of exposure to, and infection by ZIKV comprise specific peptides, isolated and non-isolated, which are strongly reactive with, and specific for ZIKV, i.e., reactive and specific epitopes of antibodies to ZIKV.

One such peptide was identified in the NS2B region of ZIKV. It is over 90% specific with ZIKV in convalescent serum samples. This peptide has the amino acid sequence:

```
                                    (SEQ ID NO: 1)
DITWEKDAEXTGNSPRLDVA,
wherein X is V or I.
```

Thus, one embodiment of the present invention is a peptide, which is reactive with, and specific for ZIKV antibodies, comprising the amino acid sequence DITWEKDAEXTGNSPRLDVA, wherein X is V or I (SEQ ID NO: 1).

Twelve other peptides were also identified along the ZIKV proteome that were over 50% specific with ZIKV antibodies in convalescent serum samples.

Thus, further embodiments of the present invention are peptides chosen from the group consisting of the twelve peptides which are reactive with, and specific for ZIKV antibodies listed in Table 2 (SEQ ID NOs: 2-13).

A further embodiment of the present invention are collections or sets of peptides comprising amino acid sequences shifted one residue across the peptide comprising the amino acid sequence DITWEKDAEXTGNSPRLDVA, wherein X is V or I (SEQ ID NO: 1) (i.e., SEQ ID NOs: 14-22). These collections or sets can comprise or consist of peptides that comprise or consist of 6 amino acids in length, 7 amino acids in length, 8 amino acids in length, 9 amino acids in length, 10 amino acids in length, 11 amino acids in length, and up to 12 amino acids in length.

A further embodiment of the present invention are collections or sets of peptides comprising amino acid sequences shifted one residue across one or more peptides chosen from the group consisting of the twelve peptides that are reactive with, and specific for ZIKV antibodies listed in Table 2 (SEQ ID NOs: 2-13). These collections or sets can comprise or consist of peptides that comprise or consist of 6 amino acids in length, 7 amino acids in length, 8 amino acids in length, 9 amino acids in length, 10 amino acids in length, 11 amino acids in length, and up to 12 amino acids in length.

In one embodiment, the collection or set of peptides includes all of the peptides comprising or consisting of the amino acid sequences shifted one residue across all of the thirteen peptides (SEQ ID NOs: 1-13) which are reactive with, and specific for ZIKV antibodies.

These various collections or sets of peptides can comprise or consist of peptides that comprise or consist of 6 amino acids in length, 7 amino acids in length, 8 amino acids in length, 9 amino acids in length, 10 amino acids in length, 11 amino acids in length, and up to 12 amino acids in length or longer.

The number of peptides used in the present invention can range from 2 peptides to a number in the thousands to tens of thousands to hundreds of thousands.

In another aspect, the invention provides compositions comprising two or more peptides of the invention.

In another aspect, the invention provides nucleic acids comprising a sequence encoding a peptide of the invention. In addition, the invention provides vectors comprising such nucleic acids, and host cells comprising such vectors. In certain embodiments, the vector is a shuttle vector. In other embodiments, the vector is an expression vector (e.g., a bacterial or eukaryotic expression vector). In certain embodiments, the host cell is a bacterial cell. In other embodiments, the host cell is a eukaryotic cell.

In non-limiting examples, the antibodies to ZIKV can be detected using any number of immunodetection techniques, which include but are not necessarily limited to Western blot, enzyme-linked immunosorbent assay (ELISA), lateral flow, dipstick type of assay or a SNAP test, multiplex antibody detection techniques of various kinds, or any modification of such assays that are suitable for detecting antibodies of interest. The patient antibody to ZIKV can be an IgG or IgA, or other immunoglobulin classes or subtypes.

In one embodiment, the immunodetection technique is in the form of a programmable peptide array.

In certain embodiments, peptides of the invention are attached to or immobilized on a solid support. In one embodiment, the peptides of the invention are attached to a solid support through a metallic nanolayer. In certain embodiments, the solid support is a bead (e.g., a colloidal particle, metallic nanoparticle or nanoshell, or latex bead), a flow path in a lateral flow immunoassay device (e.g., a porous membrane), a blot (e.g., Western blot, a slot blot, or dot blot), a flow path in an analytical or centrifugal rotor, or a tube or well (e.g., in a plate suitable for an ELISA assay or microarray). In certain embodiments, peptides of the invention are isolated (e.g., synthetic and/or purified) peptides. In certain embodiments, peptides of the invention are conjugated to a ligand. For example, in certain embodiments, the peptides are biotinylated. In other embodiments, the peptides are conjugated to streptavidin, avidin, or neutravidin. In other embodiments, the peptides are conjugated to a carrier protein (e.g., serum albumin, keyhole limpet hemocyanin (KLH), or an immunoglobulin Fc domain).

One particular embodiment of the present invention is a peptide microarray comprising peptides, which are reactive with, and specific for ZIKV antibodies. In some embodiments the peptide microarray comprises: the peptide comprising the amino acid sequence DITWEKDAEXTGNSPRLDVA, wherein X is V or I (SEQ ID NO: 1); or a peptide chosen from the group consisting of the twelve peptides listed in Table 2 (SEQ ID NOs: 2-13); or a collection or set of peptides comprising amino acid sequences shifted one residue across the peptide comprising the amino acid sequence DITWEKDAEXTGNSPRLDVA, wherein X is V or I (SEQ ID NO: 1) (i.e., SEQ ID NOs: 14-22); or a collection or set of peptides comprising amino acid sequences shifted one residue across one or more peptides chosen from the group consisting of the twelve peptides listed in Table 2 (SEQ ID NOs: 2-13); or combinations thereof.

In another aspect, the invention provides devices. In certain embodiments, the devices are useful for performing an immunoassay. For example, in certain embodiments, the device is a lateral flow immunoassay device. In other embodiments, the device is an analytical or centrifugal rotor. In other embodiments, the device is a tube or a well, e.g., in a plate suitable for an ELISA assay or a microarray. In still other embodiments, the device is an electrochemical, optical, or opto-electronic sensor.

In certain embodiments, the device comprises at least one peptide of the invention. In other embodiments, the device comprises a collection or set of the peptides of the invention as described herein. In certain embodiments, the peptides are attached to or immobilized upon the device.

In another aspect, the invention provides methods of detecting in a sample an antibody to an epitope of a Zika antigen. In certain embodiments, the methods comprise contacting a sample with one or more peptides of the invention, and detecting formation of an antibody-peptide complex comprising said peptide, wherein formation of said complex is indicative of the presence of an antibody to an epitope of a Zika antigen in said sample. In certain embodiments, the methods comprise contacting the sample with a collection or set of different peptides of the invention. In certain embodiments, the methods comprise contacting the sample with a collection or set of all of the peptides of the invention.

A further embodiment of the present invention is a method for the serological detection of exposure to and/or infection by ZIKV, comprising the use of a peptide or peptides which are reactive with, and specific for ZIKV antibodies comprising: the peptide comprising the amino acid sequence DITWEKDAEXTGNSPRLDVA, wherein X is V or I (SEQ ID NO: 1); or a peptide chosen from the group consisting of the twelve peptides listed in Table 2 (SEQ ID NOs: 2-13); or a collection or set of peptides comprising amino acid sequences shifted one residue across the peptide comprising the amino acid sequence DITWEKDAEXTGNSPRLDVA, wherein X is V or I (SEQ ID NO: 1) (i.e., SEQ ID NOs: 14-22); or a collection or set of peptides comprising amino acid sequences shifted one residue across at least one peptide chosen from the group consisting of the twelve peptides listed in Table 2 (SEQ ID NOs: 2-13); or combinations thereof.

In further embodiments of the present invention, the method for the serological detection of exposure to and/or infection by ZIKV in a sample, comprises: contacting the sample with a peptide or peptide which are reactive with, and specific for ZIKV antibodies comprising: a peptide comprising the amino acid sequence DITWEKDAEXTGNSPRLDVA, wherein X is V or I (SEQ ID NO: 1); or a peptide chosen from the group consisting of the twelve peptides listed in Table 2 (SEQ ID NOs: 2-13); or a collection or set of peptides comprising amino acid sequences shifted one residue across the peptide comprising the amino acid sequence DITWEKDAEXTGNSPRLDVA, wherein X is V or I (SEQ ID NO: 1) (i.e., SEQ ID NOs: 14-22); or a collection or set of peptides comprising amino acid sequences shifted one residue across at least one peptide chosen from the group consisting of the twelve peptides listed in Table 2 (SEQ ID NOs: 2-13); or combinations thereof; and detecting the binding between the anti-ZIKV antibodies in the sample and the peptide or peptides.

In certain embodiments, the peptide or each peptide in the collection or set is an isolated (e.g., synthetic and/or purified) peptide. In certain embodiments, the peptide or collection or set of peptides is attached to or immobilized upon a solid support. In one embodiment, the peptide or collection or set of peptides is attached to the solid support through a metallic (e.g., gold) nanolayer. In certain embodiments, the solid support is a bead or plurality of beads (e.g., a colloidal particle, a metallic nanoparticle or nanoshell, or a latex bead), a flow path in a lateral flow immunoassay device (e.g., a porous membrane), a flow path in an analytical or centrifugal rotor, a blot (e.g., Western blot, a slot blot, or dot blot), or a tube or a well (e.g., in a plate suitable for an ELISA assay or microarray). In certain embodiments, the solid support comprises metal, glass, a cellulose-based material (e.g., nitrocellulose), or a polymer (e.g., polystyrene, polyethylene, polypropylene, polyester, nylon, or polysulfone).

A further embodiment of the present invention is a method for the serological detection of exposure to and/or infection by ZIKV, comprising the use of peptide microarray comprising peptides which are reactive with, and specific for ZIKV antibodies comprising: the peptide comprising the amino acid sequence DITWEKDAEXTGNSPRLDVA, wherein X is V or I (SEQ ID NO: 1); or a peptide chosen from the group consisting of the twelve peptides listed in Table 2 (SEQ ID NOs: 2-13); or a collection or set of peptides comprising amino acid sequences shifted one residue across the peptide comprising the amino acid sequence DITWEKDAEXTGNSPRLDVA, wherein X is V or I (SEQ ID NO: 1) (i.e., SEQ ID NOs: 14-22); or a collection or set of peptides comprising amino acid sequences shifted one residue across at least one peptide chosen from the group consisting of the twelve peptides listed in Table 2 (SEQ ID NOs: 2-13); or combinations thereof.

In yet further embodiments of the present invention, the method for the serological detection of exposure to and/or infection by ZIKV in a sample, comprises: contacting the sample with a peptide microarray comprising peptides which are reactive with, and specific for ZIKV antibodies comprising: a peptide comprising the amino acid sequence DITWEKDAEXTGNSPRLDVA, wherein X is V or I (SEQ ID NO: 1); or a peptide chosen from the group consisting of the twelve peptides listed in Table 2 (SEQ ID NOs: 2-13); or a collection or set of peptides comprising amino acid sequences shifted one residue across the peptide comprising the amino acid sequence DITWEKDAEXTGNSPRLDVA, wherein X is V or I (SEQ ID NO: 1) (i.e., SEQ ID NOs: 14-22); or a collection or set of peptides comprising amino acid sequences shifted one residue across at least one peptide chosen from the group consisting of the twelve peptides listed in Table 2 (SEQ ID NOs: 2-13) or combinations thereof; and detecting the binding between the anti-ZIKV antibodies in the sample and the peptide or peptides in the microarray.

In certain embodiments, the detecting step comprises performing an ELISA assay. In other embodiments, the detecting step comprises performing a lateral flow immunoassay. In other embodiments, the detecting step comprises performing an agglutination assay. In other embodiments, the detecting step comprises spinning the sample in an analytical or centrifugal rotor. In other embodiments, the detecting step comprises analyzing the sample using a Western blot, a slot blot, or a dot blot. In still other embodiments, the detecting step comprises analyzing the sample with an electrochemical sensor, an optical sensor, or an opto-electronic sensor. In certain embodiments, the detecting step comprises performing a wavelength shift assay.

In some embodiments, the peptides consist of the amino acid sequences SEQ ID NOs: 1-13.

In some embodiments, the collection or set of peptides comprising amino acid sequences shifted one residue across the peptide comprising the amino acid sequence DITWEKDAEXTGNSPRLDVA, wherein X is V or I (SEQ ID NO: 1) comprise 12-mer peptides comprising or consisting of the amino acid sequences SEQ ID NOs: 14-22.

The present invention also includes systems and kits for the serological detection of exposure to and/or infection by ZIKV.

BRIEF DESCRIPTION OF THE FIGURES

For the purpose of illustrating the invention, there are depicted in drawings certain embodiments of the invention. However, the invention is not limited to the precise arrangements and instrumentalities of the embodiments depicted in the drawings.

DETAILED DESCRIPTION OF THE INVENTION

Definitions

Figure 1A:
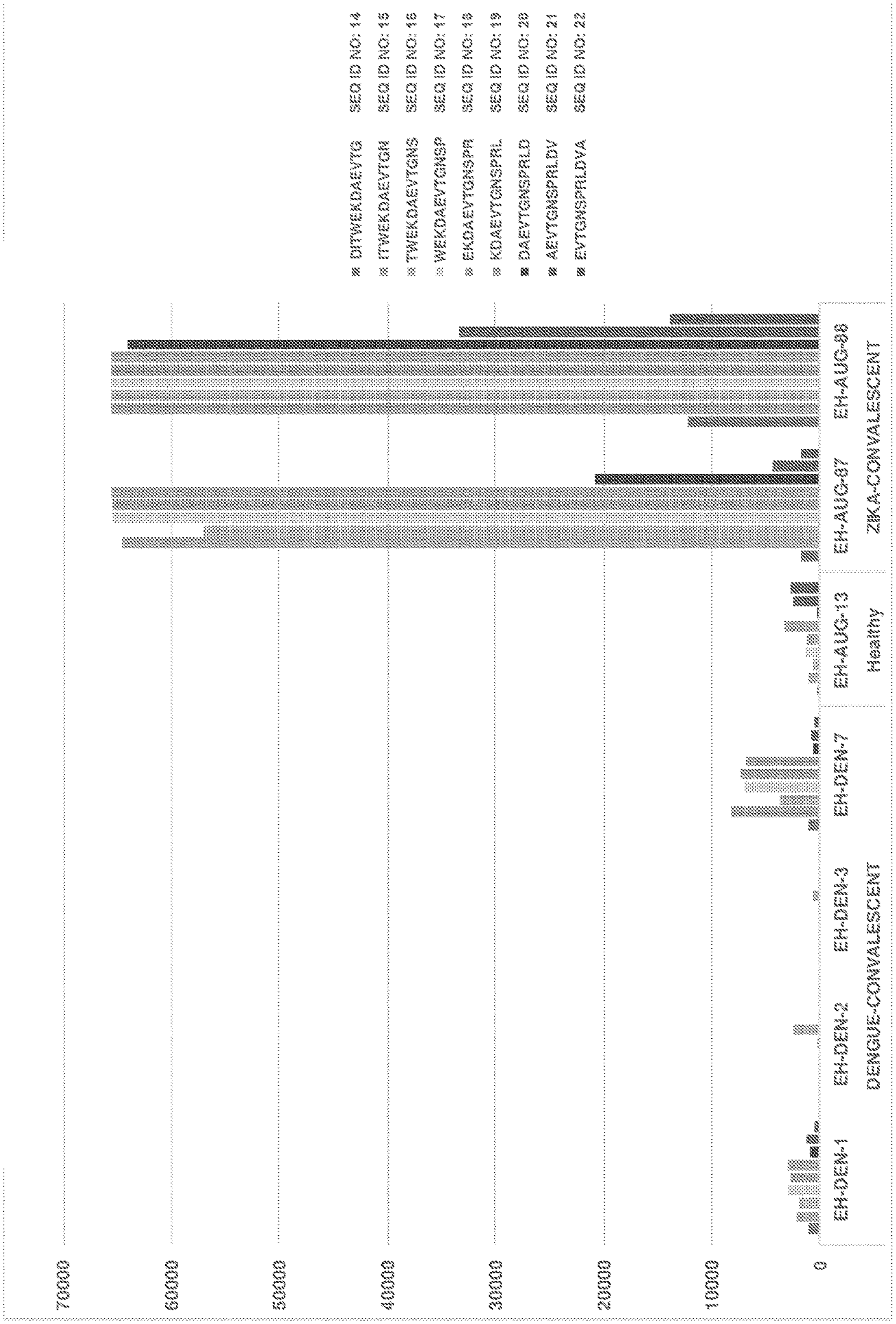
FIG. 1A is a bar diagram showing that the immunoreactive peptide (SEQ ID NO: 1) is specific and discriminatory immunoreactive epitope for Zika virus in NS2B region and the set of peptides (SEQ ID NOs: 14-22) shifted one residue across the peptide comprising the amino acid sequence DITWEKDAEVTGNSPRLDVA (SEQ ID NO: 1) are also specific and discriminatory for the Zika virus. Each bar for each sample represents SEQ ID NOs: 14-22.

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

As used herein, the term "sample" means any substance containing or presumed to contain antibodies, in particular those to ZIKV. The sample can be of natural or synthetic origin and can be obtained by any means known to those of skill in the art. The sample can be a sample of tissue or fluid isolated from a subject including but not limited to, plasma, serum, whole blood, spinal fluid, semen, amniotic fluid, lymph fluid, synovial fluid, urine, tears, blood cells, organs, and tissue. Samples can be research, clinical, or environmental. Sample can also be blood products used to transfuse or treat. Samples can also be synthetic and include but are not limited to in vitro cell culture constituents including but not limited to conditioned medium, recombinant cells, and cell components.

As used herein, the term "subject" means any organism including, without limitation, a mammal such as a mouse, a rat, a dog, a guinea pig, a ferret, a rabbit and a primate. In the preferred embodiment, the subject is a human being, a pet or livestock animal.

The term "patient" as used in this application means a human subject.

The term "detection", "detect", "detecting" and the like as used herein means as used herein means to discover the presence or existence of.

The terms "identification", "identify", "identifying" and the like as used herein means to recognize exposure to a specific virus or viruses in sample from a subject.

The term "peptide" includes any sequence of two or more amino acids. Peptide sequences specifically recited herein are written with the amino terminus on the left and the carboxy terminus on the right.

The term "amino acid," includes the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate, hippuric acid, octahydroindole-2-carboxylic acid, statine, 1,2,3,4,-tetrahydroisoquinoline-3-carboxylic acid, penicillamine, omithine, citruline, alpha-methylalanine, para-benzoylphenylalanine, phenylglycine, propargylglycine, sarcosine, and tert-butylglycine). The term also includes natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$) alkyl, phenyl or benzyl ester or amide).

An "antigen" (from antibody-generating) or "immunogen" is a substance that prompts the generation of antibodies and can cause an immune response. They may also be used for diagnostic or patient selection or characterization purposes.

Antibodies (also known as immunoglobulins (Ig)) are globulin proteins that are found in blood or other bodily fluids of vertebrates, and are used by the immune system to identify and neutralize foreign objects, such as bacteria and viruses. They are typically made of basic structural units—each with two large heavy chains and two small light chains—to form, for example, monomers with one unit, dimers with two units or pentamers with five units. Antibodies are produced by B cells. There are several different types of antibody heavy chains, and several different kinds of antibodies, which are grouped into different isotypes based on which heavy chain they possess. Five different antibody isotypes are known in mammals, which perform different roles, and help direct the appropriate immune response for each different type of foreign object they encounter.

Although the general structure of all antibodies is very similar, a small region at the tip of the protein is extremely variable, allowing millions of antibodies with slightly different tip structures to exist. This region is known as the hypervariable region. Each of these variants can bind to a different target, known as an antigen. This huge diversity of antibodies allows the immune system to recognize an equally wide diversity of antigens. The part of the antigen recognized by an antibody is termed an "epitope." These epitopes bind with their antibody in a highly specific interaction, called induced fit, which allows antibodies to identify and bind only their specific epitope in the matching antigen (s) in the midst of the millions of different molecules that make up an organism. Recognition of an antigen by an antibody tags it for attack by other parts of the immune system. Antibodies can also neutralize targets directly by, for example, binding to a part of a pathogen that it needs to cause an infection. Production of antibodies is the main function of the humoral immune system.

As used herein, the term "isolated" and the like means that the referenced material is free of components found in the natural environment in which the material is normally found. In particular, isolated biological material is free of cellular components. An isolated peptide or protein may be associated with other proteins or nucleic acids, or both, with which it associates in the cell, or with cellular membranes if it is a membrane-associated protein. An isolated material may be, but need not be, purified.

The term "substantially purified," as used herein, refers to a molecule, such as a peptide, that is substantially free of cellular material (proteins, lipids, carbohydrates, nucleic acids), culture medium, chemical precursors, chemicals used in synthesis of the peptide, or combinations thereof. A peptide that is substantially purified has less than about 40%, 30%, 25%, 20%, 15%, 10%, 5%, 2%, 1% or less of the cellular material, culture medium, other polypeptides, chemical precursors, and/or chemicals used in synthesis of the peptide. Accordingly, a substantially pure molecule, such as a peptide, can be at least about 60%, 70%, 75%, 80%, 85%, 90%, 95%, 98%, or 99%, by dry weight, the molecule of interest.

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

The current invention enhances the differential diagnosis and management of ZIKV by establishing a new serologic assay platform for profiling a subject's pathogen exposure history.

In contrast to molecular diagnostics where advances in technology such as polymeraase chain reaction and high-throughput screening have dramatically improved sensitivity, specificity and breadth over the past 20 years, serologic methods remained largely unchanged. This lag is important given the role of serology in establishing the distribution and frequency of infection, testing the significance of association between the finding of an agent and disease, and in focusing efforts in pathogen discovery. Described herein is the first sensitive, unbiased, highly multiplexed platform for diagnostic serology of ZIKV in particular. This peptide array-based platform will enable new strategies for investigating the epidemiology and pathogenesis of acute and chronic diseases due to infection and for monitoring humoral responses to vaccines and immunomodulatory drugs. It will also serve as a screening tool for rapid selection of key informative peptides that can be used in established, inexpensive, alternative platforms including lateral flow immunoassays. Such applications will have practical utility for both clinical medicine and public health by enabling retrospective differential diagnosis of an infectious illness (when genetic footprints of the agent may no longer be present), and in facilitating outbreak investigation and surveillance.

This is particularly useful in infection by ZIKV as a patient could no longer have the evidence of acute infection, e.g., viral nucleic acids, but have had a ZIKV infection in the past that could affect an unborn child or be the cause of another illness, e.g., Guillain-Barré syndrome.

The current invention is an assay that was developed using the strategy of tiling the viral proteome in a sliding window of 12-mer peptides that shifted one residue (e.g. residues 1-12, 2-13, 3-14). The goal was to obtain peptides that are specific and sensitive for Zika. Such a peptide was obtained from the NS2B region of Zika virus, which is specific and about 85% sensitive for detection of antibodies in patients with a documented history of ZIKV infection. The same tiling strategy can be used to synthesize shorter peptides, (6, 7, 8, 9 or 10 amino acids in length) corresponding to the other regions of the ZIKV proteome, including the NS1 and envelope proteins.

Isolated Peptides Specific and Sensitive for ZIKV Antibodies (ZIKV Reactive Peptides)

The present invention includes isolated peptides which are strongly reactive with, and sensitive to antibodies to ZIKV in a patient sample. These peptides can be used in any type of serological assay or platform, now known or later developed, to screen for the presence of antibodies to ZIKV and to determine if a subject has had an infection by and/or exposure to ZIKV. These peptides can also be used to test for and monitor humoral responses to vaccines and immunomodulatory drugs, thus, being useful for the development of treatment and preventative agents for ZIKV.

One embodiment of the present invention is an isolated peptide identified in the NS2B region of ZIKV at 1426-1434 of Accession ZIKV_AY632535_AAV34151, and has the amino acid sequence of 1426-DITWEKDAEVTGNSPRLDVA-1434 (SEQ ID NO: 1). This peptide was identified as shown in the Experimental Examples and is over 90% specific with Zika convalescent serum samples.

Additionally, a few Zika viruses have a mutation wherein the valine at amino acid 1439 is isoleucine, i.e., 1426-DITWEKDAEITGNSPRLDVA-1434 (SEQ ID NO: 1). Peptides with this mutation were tested as set forth below and the mutation did not affect peptide array or ELISA results (see FIG. 1). Thus the isolated peptide identified as described herein can have either valine or isoleucine at position 10 and the reactivity and specificity remain the same.

A further embodiment of the present invention comprises a collection or set of peptides comprising amino acid sequences shifted one residue across the peptide comprising the amino acid sequence DITWEKDAEXTGNSPRLDVA, wherein X is V or I (SEQ ID NO: 1). This collection or can contain peptides that are 6 amino acids in length, 7 amino acids in length, 8 amino acids in length, 9 amino acids in length, 10 amino acids in length, 11 amino acids in length, and up to 12 amino acids in length.

In one embodiment, each peptide in the set or collection is 12 amino acids in length. The collection of peptides includes peptides with the following amino acid sequences:

```
                              (SEQ ID NO: 14)
DITWEKDAEXTG;
wherein X is V or I

                              (SEQ ID NO: 15)
ITWEKDAEXTGN;
wherein X is V or I

                              (SEQ ID NO: 16)
TWEKDAEXTGNS;
wherein X is V or I

                              (SEQ ID NO: 17)
WEKDAEXTGNSP;
wherein X is V or I

                              (SEQ ID NO: 18)
EKDAEXTGNSPR;
wherein X is V or I

                              (SEQ ID NO: 19)
KDAEXTGNSPRL;
wherein X is V or I

                              (SEQ ID NO: 20)
DAEXTGNSPRLD;
wherein X is V or I

                              (SEQ ID NO: 21)
AEXTGNSPRLDV;
wherein X is V or I
and

                              (SEQ ID NO: 22)
EXTGNSPRLDVA
wherein X is V or I
```

The present invention also includes twelve additional isolated peptides that are over 50% specific with Zika convalescent serum samples.

These additional isolated peptides are listed in Table 2 and comprise SEQ ID NOs 2-13.

Other embodiments of the present invention include a collection or set of isolated peptides comprising or consisting of amino acid sequences shifted one residue across one, two, three, four, five, six, seven, eight, nine, ten, eleven or all twelve of these twelve peptides.

This collection or set can comprise or consist of isolated peptides comprising or consisting of 6 amino acids in length, 7 amino acids in length, 8 amino acids in length, 9 amino acids in length, 10 amino acids in length, 11 amino acids in length, and up to 12 amino acids in length.

Peptides of 12 amino acids are preferred based upon work that shows that antibodies bind to linear peptide sequences ranging from 5 to 9 amino acids in length and bind most efficiently when targets are flanked by additional amino acids (Buus et al. 2012). However, peptides containing less than 12 amino acids in length and more than 12 amino acids in length can be used. Peptides 13 amino acids in length, 14 amino acids in length, 15 amino acids in length, 16 amino acids in length, 17 amino acids in length, 18 amino acids in length, 19 amino acids in length, 20 amino acids in length, up to 25 amino acids in length, up to 30 amino acids in length, up to 35 amino acids in length, up to 40 amino acids in length, and up to 50 amino acids in length can be used.

In certain embodiments, peptides of the invention are produced by synthetic chemistry (i.e., a "synthetic peptide"). In other embodiments, peptides of the invention are produced biologically. An isolated peptide of the invention can be in water, a buffer, or in a dry form awaiting reconstitution, e.g., as part of a kit. An isolated peptide of the present invention can be in the form of a pharmaceutically acceptable salt. Suitable acids and bases that are capable of forming salts with the peptides of the present invention are well known to those of skill in the art, and include inorganic and organic acids and bases.

In certain embodiments, peptides of the invention are modified. The peptides of the invention may be modified by a variety of techniques, such as by denaturation with heat and/or a detergent (e.g., SDS). Alternatively, peptides of the invention may be modified by association with one or more further moieties. The association can be covalent or non-covalent, and can be, for example, via a terminal amino acid linker, such as lysine or cysteine, a chemical coupling agent, or a peptide bond. The additional moiety can be, for example, a ligand, a ligand receptor, a fusion partner, a detectable label, an enzyme, or a substrate that immobilizes the peptide.

Peptides of the invention can be conjugated to a ligand, such as biotin (e.g., via a cysteine or lysine residue), a lipid molecule (e.g., via a cysteine residue), or a carrier protein (e.g., serum albumin, immunoglobulin Fc domain, keyhole limpet hemocyanin (KLH) via e.g., a cysteine or lysine residue). Attachment to ligands, such as biotin, can be useful for associating the peptide with ligand receptors, such as avidin, streptavidin, polymeric streptavidin, or neutravidin. Avidin, streptavidin, polymeric streptavidin, or neutravidin, in turn, can be linked to a signaling moiety (e.g., an enzyme, such as horse radish peroxidase (HRP) or alkaline phosphatase (ALP), or other moiety that can be visualized, such as a metallic nanoparticle or nanoshell (e.g., colloidal gold) or a fluorescent moiety), or a solid substrate (e.g., nitrocellulose membrane). Alternatively, the peptides of the invention can be fused or linked to a ligand receptor, such as avidin, streptavidin, polymeric streptavidin, or neutravidin, thereby facilitating the association of the peptides with the corresponding ligand, such as biotin and any moiety (e.g., signaling moiety) or solid substrate attached thereto. Examples of other ligand-receptor pairs are well-known in the art and can similarly be used.

Peptides of the invention can be fused to a fusion partner (e.g., a peptide or other moiety) that can be used to improve purification, to enhance expression of the peptide in a host cell, to aid in detection, and to stabilize the peptide. Examples of suitable compounds for fusion partners include carrier proteins (e.g., serum albumin, immunoglobulin Fc domain, KLH), and enzymes (e.g., horse radish peroxidase (HRP), beta-galactosidase, glutathione-S-transferase, alkaline phosphatase). The fusion can be achieved by means of a peptide bond. For example, peptides of the invention and fusion partners can be fusion proteins and can be directly fused in-frame or can comprise a peptide linker.

In addition, peptides of the invention may be modified to include any of a variety of known chemical groups or molecules. Such modifications include, but are not limited to, glycosylation, acetylation, acylation, ADP-ribosylation, amidation, covalent attachment to polyethylene glycol (e.g., PEGylation), covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, ubiquitination, modifications with fatty acids, and transfer-RNA mediated addition of amino acids to proteins such as arginylation. Analogues of an amino acid (including unnatural amino acids) and peptides with substituted linkages are also included. Peptides of the invention that consist of any of the sequences discussed herein may be modified by any of the discussed modifications. Such peptides still "comprise" or "consist of" the amino acids.

Modifications as set forth above are well-known to those of skill in the art and have been described in great detail in the scientific literature.

Nucleic Acids Comprising a Sequence Encoding the ZIKV Reactive Peptides

In another aspect, the invention provides nucleic acids comprising a sequence encoding a peptide of the invention. Nucleic acids of the invention can be single- or double-stranded. A nucleic acid can be RNA, DNA, cDNA, genomic DNA, chemically synthesized RNA or DNA or combinations thereof. The nucleic acids can be purified free of other components, such as proteins, lipids and other polynucleotides. For example, the nucleic acids can be 50%, 75%, 90%, 95%, 96%, 97%, 98%, 99%, or 100% purified. The nucleic acids of the invention encode the peptides described herein. In certain embodiments, the nucleic acids encode a peptide having the sequence of SEQ ID NOs: 1-24. Nucleic acids of the invention can comprise other nucleotide sequences, such as sequences coding for linkers, signal sequences, TMR stop transfer sequences, transmembrane domains, or ligands useful in protein purification such as glutathione-S-transferase, histidine tag, and staphylococcal protein A.

Methods for preparing polynucleotides operably linked to an expression control sequence and expressing them in a host cell are well-known in the art. See, e.g., U.S. Pat. No. 4,366,246. A nucleic acid of the invention is operably linked when it is positioned adjacent to or close to one or more expression control elements, which direct transcription and/or translation of the polynucleotide.

Thus, for example, the peptides of the invention can be produced recombinantly following conventional genetic engineering techniques. To produce a recombinant peptide of the invention, a nucleic acid encoding the peptide is inserted into a suitable expression system. Generally, a recombinant molecule or vector is constructed in which the polynucleotide sequence encoding the selected peptide is operably linked to an expression control sequence permitting expression of the peptide. Numerous types of appropriate expression vectors are known in the art, including, e.g., vectors containing bacterial, viral, yeast, fungal, insect or mammalian expression systems. Methods for obtaining and using such expression vectors are well-known. For guidance in this and other molecular biology techniques used for compositions or methods of the invention, see, e.g., Sambrook et al., Molecular Cloning, A Laboratory Manual, current edition, Cold Spring Harbor Laboratory, New York; Miller et al, Genetic Engineering, 8:277-298 (Plenum Press, current edition), Wu et al., Methods in Gene Biotechnology (CRC Press, New York, N.Y., current edition), Recombinant Gene Expression Protocols, in Methods in Molecular Biology, Vol. 62, (Tuan, ed., Humana Press, Totowa, N.J., current edition), and Current Protocols in Molecular Biology, (Ausabel et al., Eds.,) John Wiley & Sons, NY (current edition), and references cited therein.

Accordingly, the invention also provides vectors comprising nucleic acids of the invention, and host cells comprising such vectors. In certain embodiments, the vector is a shuttle vector. In other embodiments, the vector is an expression vector (e.g., a bacterial or eukaryotic expression vector). In certain embodiments, the host cell is a bacterial cell. In other embodiments, the host cell is a eukaryotic cell.

Platforms, Assays and Device for Using the ZIKV Reactive Peptides

There are a number of different conventional assays for detecting formation of an antibody-peptide complex comprising a peptide or peptides of the invention. For example, the detecting step can comprise performing an ELISA assay, performing an immunofluorescence assay, performing a lateral flow immunoassay, performing an agglutination assay, performing a wavelength shift assay, performing a Western blot, slot blot, or dot blot, analyzing the sample in an analytical or centrifugal rotor, or analyzing the sample with an electrochemical, optical, or opto-electronic sensor. These different assays are described herein and/or are well-known to those skilled in the art.

Thus, the peptides of the present invention can be used in any assay, format or platform for antibody detection including but not limited to ELISA, Luminex, Western blot assays, and spotted peptide arrays, as well as those platforms that are later developed.

In certain embodiments of the invention, the assay comprises—immobilizing the antibody(s) in the sample; adding a peptide of the invention; and detecting the degree of antibody bound to the peptide, e.g., by the peptide being labeled or by adding a labeled substance, such as a labeled binding partner (e.g., streptavidin-HRP or streptavidin-colloidal gold complex) or a labeled antibody which specifically recognizes the peptide.

In other embodiments, the assay comprises: immobilizing a peptide of the invention; adding the sample containing antibodies; and detecting the amount of antibody bound to the peptide, e.g., by adding another peptide of the invention conjugated, directly or indirectly, to a label (e.g., metallic nanoparticle or metallic nanoshell, fluorescent label, or enzyme (e.g., horseradish peroxidase or alkaline phosphatase)) or by adding a labeled substance, such as a binding partner or a labeled antibody which specifically recognizes the sample antibodies (e.g., anti-human IgG antibodies, or anti-human IgM antibodies).

In other embodiments, the assay comprises: immobilizing a peptide of the invention; adding the sample containing antibodies; and detecting the amount of antibody bound to the peptide, e.g., by adding a first binding partner which specifically recognizes the sample antibodies (e.g., anti-human IgG antibodies, or anti-human IgM antibodies), and further adding a second binding partner, wherein the second binding partner is labeled and recognizes said first binding partner.

In still other embodiments, the assay comprises: reacting the peptide and the sample containing antibodies without any of the reactants being immobilized, and then detecting the amount of complexes of antibody and peptide, e.g., by the peptide being labeled or by adding a labeled substance, such as a labeled binding partner (e.g., streptavidin-HRP or streptavidin-colloidal gold complex) or a labeled antibody which specifically recognizes the peptide.

Immobilization of a peptide of the invention can be either covalent or non-covalent, and the non-covalent immobilization can be non-specific (e.g., non-specific binding to a polystyrene surface in a microtiter well). Specific or semi-specific binding to a solid or semi-solid carrier, support or surface, can be achieved by the peptide having, associated with it, a moiety which enables its covalent or non-covalent binding to the solid or semi-solid carrier, support or surface. For example, the moiety can have affinity to a component attached to the carrier, support or surface. In this case, the moiety may be, for example, a biotin or biotinyl group or an analogue thereof bound to an amino acid group of the peptide, and the component is then avidin, streptavidin, neutravidin, or an analogue thereof.

Suitable carriers, supports, and surfaces include, but are not limited to, metallic nanolayers, beads (e.g., magnetic beads, colloidal particles or metallic nanoparticles or nanoshells, such as colloidal gold, or particles or nanoparticles comprising silica, latex, polystyrene, polycarbonate, or PDVF), latex of co-polymers such as styrene-divinyl benzene, hydroxylated styrene-divinyl benzene, polystyrene, carboxylated polystyrene, beads of carbon black, non-activated or polystyrene or polyvinyl chloride activated glass, epoxy-activated porous magnetic glass, gelatin or polysaccharide particles or other protein particles, red blood cells, mono- or polyclonal antibodies or Fab fragments of such antibodies.

The protocols for immunoassays using antigens for detection of specific antibodies are well known in art. For example, a conventional sandwich assay can be used, or a conventional competitive assay format can be used.

Devices for performing specific binding assays, especially immunoassays, are known and can be readily adapted for use in the present methods. Solid-phase assay devices include microtiter plates, flow-through assay devices (e.g., lateral flow immunoassay devices), dipsticks, and immunocapillary or immunochromatographic immunoassay devices.

In embodiments of the invention, the solid or semi-solid surface or carrier is the floor or wall in a microtiter well, a filter surface or membrane (e.g., a nitrocellulose membrane or a PVDF (polyvinylidene fluoride) membrane), a hollow fiber, a beaded chromatographic medium (e.g., an agarose or polyacrylamide gel), a magnetic bead, a fibrous cellulose matrix, an HPLC matrix, an FPLC matrix, a substance having molecules of such a size that the molecules with the peptide bound thereto, when dissolved or dispersed in a liquid phase, can be retained by means of a filter, a substance capable of forming micelles or participating in the formation of micelles allowing a liquid phase to be changed or exchanged without entraining the micelles, a water-soluble polymer, or any other suitable carrier, support or surface.

In some embodiments of the invention, the peptide of the invention is provided with a suitable label which enables detection. Conventional labels may be used which are capable, alone or in concert with other compositions or compounds, of providing a detectable signal. Suitable labels include, but are not limited to, enzymes (e.g., HRP, beta-galactosidase, or alkaline phosphatase), fluorescent labels, radioactive labels, colored latex particles, and metal-conjugated labels (e.g., metallic nanolayers, metallic nanoparticle- or metallic nanoshell-conjugated labels). Suitable metallic nanoparticle or metallic nanoshell labels include, but are not limited to, gold particles, silver particles, copper particles, platinum particles, cadmium particles, composite particles, gold hollow spheres, gold-coated silica nanoshells, and silica-coated gold shells. Metallic nanolayers suitable for detectable layers include nanolayers comprised of cadmium, zinc, mercury, and noble metals, such as gold, silver, copper, and platinum.

Suitable detection methods include, but are not limited to, detection of an agent which is tagged, directly or indirectly, with a colorimetric assay (e.g., for detection of HRP or beta-galactosidase activity), visual inspection using light microscopy, immunofluorescence microscopy, including confocal microscopy, or by flow cytometry (FACS), autoradiography (e.g., for detection of a radioactively labeled agent), electron microscopy, immunostaining, subcellular fractionation, or the like. In one embodiment, a radioactive element (e.g., a radioactive amino acid) is incorporated directly into a peptide chain. In another embodiment, a fluorescent label is associated with a peptide via biotin/avidin interaction, association with a fluorescein conjugated antibody, or the like. In one embodiment, a detectable specific binding partner for the antibody is added to the mixture. For example, the binding partner can be a detectable secondary antibody or other binding agent (e.g., protein A, protein G, protein L or combinations thereof) which binds to the first antibody. This secondary antibody or other binding agent can be labeled with, for example, a radioactive, enzymatic, fluorescent, luminescent, metallic nanoparticle or metallic nanoshell (e.g. colloidal gold), or other detectable label, such as an avidin/biotin system. In another embodiment, the binding partner is a peptide of the invention, which can be conjugated directly or indirectly to an enzyme, such as horseradish peroxidase or alkaline phosphatase or other signaling moiety. In such embodiments, the detectable signal is produced by adding a substrate of the enzyme that produces a detectable signal, such as a chromogenic, fluorogenic, or chemiluminescent substrate.

In some embodiments of the invention, the detection procedure comprises visibly inspecting the antibody-peptide complex for a color change, or inspecting the antibody-peptide complex for a physical-chemical change. Physical-chemical changes may occur with oxidation reactions or other chemical reactions. They may be detected by eye, using a spectrophotometer, or the like.

One assay format is a lateral flow immunoassay format. Antibodies to human or animal immunoglobulins, can be labeled with a signal generator or reporter (e.g., colloidal gold) that is dried and placed on a glass fiber pad (sample application pad or conjugate pad). The diagnostic peptide is immobilized on membrane, such as nitrocellulose or a PVDF (polyvinylidene fluoride) membrane. When a sample is applied to the sample application pad (or flows through the conjugate pad), it dissolves the labeled reporter, which then binds to all antibodies in the sample. The resulting complexes are then transported into the next membrane (PVDF or nitrocellulose containing the diagnostic peptide) by capillary action. If antibodies against the diagnostic peptide are present, they bind to the diagnostic peptide striped on the membrane, thereby generating a signal (e.g., a band that can be seen or visualized). An additional antibody specific to the labeled antibody or a second labeled antibody can be used to produce a control signal.

An alternative format for the lateral flow immunoassay comprises the peptides or compositions of the invention being conjugated to a ligand (e.g., biotin) and complexed with labeled ligand receptor (e.g., streptavidin-colloidal gold). The labeled peptide complexes can be placed on the sample application pad or conjugate pad. Anti-human IgG/IgM or anti-animal IgG/IgM antibodies of the invention are immobilized on a membrane, such as nitrocellulose of PVDF, at a test site. When sample is added to the sample application pad, antibodies in the sample react with the labeled peptide complexes such that antibodies that bind to peptides of the invention become indirectly labeled. The antibodies in the sample are then transported into the next membrane (PVDF or nitrocellulose containing the diagnostic peptide) by capillary action and bind to the immobilized anti-human IgG/IgM or anti-animal IgG/IgM antibodies. If any of the sample antibodies are bound to the labeled peptides of the invention, the label associated with the peptides can be seen or visualized at the test site.

Another assay for the screening of blood products or other physiological or biological fluids is an enzyme linked immunosorbent assay, i.e., an ELISA. Typically in an ELISA, isolated peptides or collection or set of peptides of the invention, are adsorbed to the surface of a microtiter well directly or through a capture matrix (e.g., an antibody). Residual, non-specific protein-binding sites on the surface are then blocked with an appropriate agent, such as bovine serum albumin (BSA), heat-inactivated normal goat serum (NGS), or BLOTTO (a buffered solution of nonfat dry milk which also contains a preservative, salts, and an antifoaming agent). The well is then incubated with a biological sample suspected of containing specific antibody. The sample can be applied neat, or more often it can be diluted, usually in a buffered solution which contains a small amount (0.1-5.0% by weight) of protein, such as BSA, NGS, or BLOTTO. After incubating for a sufficient length of time to allow specific binding to occur, the well is washed to remove unbound protein and then incubated with an optimal concentration of an appropriate anti-immunoglobulin antibody that is conjugated to an enzyme or other label by standard procedures and is dissolved in blocking buffer. The label can be chosen from a variety of enzymes, including horseradish peroxidase (HRP), beta-galactosidase, alkaline phosphatase (ALP), and glucose oxidase. Sufficient time is allowed for specific binding to occur again, then the well is washed again to remove unbound conjugate, and a suitable substrate for the enzyme is added. Color is allowed to develop and the optical density of the contents of the well is determined visually or instrumentally (measured at an appropriate wave length). Conditions for performing ELISA assays are well-known in the art.

In another embodiment of an ELISA, a peptide or a collection or set of peptides of the invention is immobilized on a surface, such as a ninety-six-well ELISA plate A sample is then added and the assay proceeds as above.

In still other embodiments, a peptide or collection or set of peptides of the invention are electro- or dot-blotted onto nitrocellulose paper. Subsequently, a sample, such as a biological fluid (e.g., serum or plasma) is incubated with the blotted antigen, and antibody in the biological fluid is allowed to bind to the antigen(s). The bound antibody can then be detected, e.g., by standard immunoenzymatic methods or by visualization using metallic nanoparticles or nanoshells coupled to secondary antibodies or other antibody binding agents or combinations thereof.

It should be understood by one of skill in the art that any number of conventional protein assay formats, particularly immunoassay formats, may be designed to utilize the isolated peptides of this invention, and collections and sets of peptides of the invention, for the detection of Zika antibodies in a subject. This invention is thus not limited by the selection of the particular assay format, and is believed to encompass assay formats that are known to those of skill in the art. To date most serology has been performed using singleplex ELISA, complement fixation or neutralization assays. More recently, Luminex-based systems have been employed that can address up to 100 antigenic targets simultaneously (i.e., 100 individual pathogens, 100 individual antigenic targets for one pathogen, or some variation thereof) (Anderson et al. 2011). Additionally, arrays are established that comprise spotted recombinant proteins expressed in vitro in *E. coli, S. cerevesiae*, baculoviruses, or cell-free, coupled transcription-translation systems (Vigil et al. 2010).

One goal of the present invention is to automate the process of ZIKV antibody detection and make it inexpensive, quick and accurate as well as detect exposure per se rather than to rigorously characterize humoral responses to specific pathogens.

One assay that meets these requirements is a programmable peptide array.

One method to create and validate a programmable array that can measure the humoral immune response to ZIKV, thus enabling detection of exposure to ZIKV (or its gene products in vaccines), comprises the following steps: 1) select viral peptides using bioinformatic methods; 2) test those peptides printed on arrays for sensitivity and specificity using sera from humans and other animals who have been exposed to antigens of ZIKV; 3) examine the performance of algorithms typically employed for epitope prediction; 4) use assay results to develop smaller and less comprehensive peptide libraries that can be deployed in smaller and more facile platforms; 5) optimize and validate assay protocols; and 6) develop software to automate assay analysis.

Using these steps, the peptides of the present invention were generated.

The peptide array capacity can be exploited to print multiple arrays per glass slide (configurations of 1, 3, 8, or 12 arrays can be printed).

Thus, one embodiment of the present invention is a peptide microarray comprising peptides that are reactive with, and specific for ZIKV antibodies. In some embodiments the peptide microarray comprises: the peptide comprising the amino acid sequence DITWEKDAEXTGNSPRLDVA, wherein X is V or I (SEQ ID NO: 1); or a peptide chosen from the group consisting of the twelve peptides listed in Table 2 (SEQ ID NOs: 2-13); or a collection or set of peptides shifted one residue across the peptide comprising the amino acid sequence DITWEKDAEXTGNSPRLDVA, wherein X is V or I (SEQ ID NO: 1) (i.e., SEQ ID NOs: 14-22); or a collection or set of peptides shifted one residue across at least one peptide chosen from the group consisting of the twelve peptides listed in Table 2 (SEQ ID NOs: 2-13); or combinations thereof.

A further embodiment of the present invention is a peptide microarray comprising a collection or set of peptides comprising the amino acid sequences SEQ ID NOs: 14-2).

In some embodiments the peptide array comprises a set or collection of peptides, comprising amino acid sequences shifted one residue across all of the peptides comprising or consisting of the amino acid sequences of SEQ ID NOs: 1-13.

Methods and Systems for Serological Detection of Exposure to ZIKV

The present invention includes methods and systems for the detection of exposure to antigens of ZIKV, i.e., antibodies to ZIKV, in any sample utilizing the various peptides, isolated and non-isolated, and peptide microarrays of the present invention.

Suitable methods typically include: receiving or obtaining (e.g., from a patient) a sample of bodily fluid or tissue likely to contain antibodies; contacting (e.g., incubating or reacting) a sample to be assayed with a peptide or peptides of the invention, under conditions effective for the formation of a specific peptide-antibody complex (e.g., for specific binding of the peptide to the antibody); and assaying the contacted (reacted) sample for the presence of an antibody-peptide reaction (e.g., determining the amount of an antibody-peptide complex). The presence of an elevated amount of the antibody-peptide complex indicates that the subject was exposed to and infected by the Zika virus. A peptide, including a modified form thereof, which "binds specifically" to an antibody against a Zika antigen interacts with the antibody, or forms or undergoes a physical association with it, in an amount and for a sufficient time to allow detection of the antibody.

Conditions for reacting peptides and antibodies so that they react specifically are well-known to those of skill in the art. See, e.g., Current Protocols in Immunology (Coligan et al., editors, John Wiley & Sons, Inc).

Once the peptide or peptides of the invention and sample antibody are permitted to react in a suitable medium, an assay is performed to determine the presence or absence of an antibody-peptide reaction. Any of the assays discussed herein can be used.

The methods and systems of the present invention may be used to detect exposure to antigens of ZIKV in research and clinical settings.

One sample for use in the methods is a biological sample. A biological sample may be obtained from a tissue of a subject or bodily fluid from a subject including but not limited to nasopharyngeal aspirate, blood, cerebrospinal fluid, saliva, serum, plasma, urine, sputum, bronchial lavage, pericardial fluid, or peritoneal fluid, or a solid such as feces. The preferred biological sample is serum, plasma and urine. The subject may be any animal, particularly a vertebrate and more particularly a mammal, including, without limitation, a cow, dog, human, monkey, mouse, pig, or rat. In one embodiment, the subject is a human.

A sample may also be a research, clinical, or environmental sample, such as cells, cell culture, cell culture medium, and compositions for use as, or the development of pharmaceutical and therapeutic agents.

Additional applications include, without limitation, detection of the screening of blood products (e.g., screening blood products for infectious agents), biodefense, food safety, environmental contamination, forensics, and genetic-comparability studies. The present invention also provides methods and systems for detecting viral antibodies in cells, cell culture, cell culture medium and other compositions used for the development of pharmaceutical and therapeutic agents.

The subject may have been exposed to antigens of ZIKV, suspected of having exposure to antigens of ZIKV or believed not to have had exposure to antigens of ZIKV. In one embodiment, the subject is a female, and in a further embodiment the female subject may be pregnant or attempting to become pregnant. In one embodiment, the subject may have been found to be seropositive by ZIKV ELISA.

In one embodiment, the subject may be a test subject, which has been administered a ZIKV vaccine or immunomodulatory agent.

The systems and methods described herein support the detection and measure of a humoral immune response to ZIKV.

One embodiment of the present invention provides a system for the detection of exposure to antigens of ZIKV, i.e., antibodies to ZIKV, in any sample. The system includes at least one subsystem, wherein the subsystem includes a peptide or peptides or a collection or set of peptides of the invention, which are reactive with, and specific for ZIKV antibodies, comprising: the peptide comprising the amino acid sequence DITWEKDAEXTGNSPRLDVA, wherein X is V or I (SEQ ID NO: 1); or a peptide chosen from the group consisting of the twelve peptides listed in Table 2 (SEQ ID NOs: 2-13); or a collection or set of peptides comprising amino acid sequences shifted one residue across the peptide comprising the amino acid sequence DITWEKDAEXTGNSPRLDVA, wherein X is V or I (SEQ ID NO: 1) (i.e., SEQ ID NOs: 14-22); or a collection or set of peptides comprising amino acid sequences shifted one residue across at least one peptide chosen from the group consisting of the twelve peptides listed in Table 2 (SEQ ID NOs: 2-13); or combinations thereof. The system can also include additional subsystems for the purpose of: preparation of the sample; binding of any ZIKV antibody in the sample with the peptides(s); washing the unbound sample; and visualization and/or quantification of bound antibody or antibodies.

A further embodiment of the present invention provides a system for the detection of exposure to antigens of ZIKV, i.e., antibodies to ZIKV, in any sample. The system includes at least one subsystem, wherein the subsystem includes a peptide microarray comprising a peptide or peptides or a collection or set of peptides of the invention, which are reactive with, and specific for ZIKV antibodies comprising: the peptide comprising the amino acid sequence DITWEKDAEXTGNSPRLDVA, wherein X is V or I (SEQ ID NO: 1); or a peptide chosen from the group consisting of the twelve peptides listed in Table 2 (SEQ ID NOs: 2-13); or a collection or set of peptides comprising amino acid sequences shifted one residue across the peptide comprising the amino acid sequence DITWEKDAEXTGNSPRLDVA, wherein X is V or I (SEQ ID NO: 1) (i.e., SEQ ID NOs: 14-22); or a collection or set of peptides comprising amino acid sequences shifted one residue across at least one peptide chosen from the group consisting of the twelve peptides listed in Table 2 (SEQ ID NOs: 2-13); or combinations thereof. The system can also include additional subsystems for the purpose of: preparation of the sample; binding of any ZIKV antibody in the sample with the peptides(s); washing the unbound sample; and visualization and/or quantification of bound antibody or antibodies.

The present invention provides a method for detecting the exposure to antigens of ZIKV, i.e., antibodies to ZIKV, in any sample, including the steps of: contacting the sample with a peptide or peptides or a collection or set of peptides of the invention, which are reactive with, and specific for ZIKV antibodies, comprising: the peptide comprising the amino acid sequence DITWEKDAEXTGNSPRLDVA, wherein X is V or I (SEQ ID NO: 1); or a peptide chosen from the group consisting of the twelve peptides listed in Table 2 (SEQ ID NOs: 2-13); or a collection or set of peptides comprising amino acid sequences shifted one residue across the peptide comprising the amino acid sequence DITWEKDAEXTGNSPRLDVA, wherein X is V or I (SEQ ID NO: 1) (i.e., SEQ ID NOs: 14-22); or a collection or set of peptides comprising amino acid sequences shifted one residue across at least one peptide chosen from the group consisting of the twelve peptides listed in Table 2 (SEQ ID NOs: 2-13); or combinations thereof, under conditions sufficient for any antibodies to ZIKV in the sample and the peptides to bind; and visualizing and/or quantifying any bound antibody or antibodies to the peptides. The method may optionally include a step for washing any unbound sample.

The present invention provides a method for the detecting the exposure to antigens of ZIKV, i.e., antibodies to ZIKV, in any sample, including the steps of: contacting the sample with a peptide microarray comprising a peptide or peptides or a collection or set of peptides of the invention, which are reactive with, and specific for ZIKV antibodies comprising: the peptide comprising the amino acid sequence DITWEKDAEXTGNSPRLDVA, wherein X is V or I (SEQ ID NO: 1); or a peptide chosen from the group consisting of the twelve peptides listed in Table 2 (SEQ ID NOs: 2-13); or a collection or set of peptides comprising amino acid sequences shifted one residue across the peptide comprising the amino acid sequence DITWEKDAEXTGNSPRLDVA, wherein X is V or I (SEQ ID NO: 1) (i.e., SEQ ID NOs: 14-22); or a collection or set of peptides comprising amino acid sequences shifted one residue across at least one peptide chosen from the group consisting of the twelve peptides listed in Table 2 (SEQ ID NOs: 2-13); or combinations thereof under conditions sufficient for any antibodies to ZIKV in the sample and the peptides to bind; and visualizing and/or quantifying any bound antibody or antibodies to the peptides. The method may optionally include a step for washing any unbound sample.

Any method of detection discussed herein or known in the art can be used for visualizing and/or quantifying the bound antibodies.

In one embodiment of the present invention, the peptides for use in the systems and methods would comprise a collection or set of peptides comprising or consisting of the amino acid sequences SEQ ID NOs: 14-22.

In one embodiment of the present invention, the peptide microarray for use in the systems and methods would comprise a collection of peptides comprising or consisting of the amino acid sequences SEQ ID NOs: 14-22.

Kits

The invention also includes reagents and kits for practicing the methods of the invention. These reagents and kits may vary.

One reagent of the kit would be a peptide or peptides or a collection or set of peptides of the invention, which are reactive with, and specific for ZIKV antibodies, comprising: the peptide comprising the amino acid sequence DITWEKDAEXTGNSPRLDVA, wherein X is V or I (SEQ ID NO: 1); or a peptide chosen from the group consisting of the twelve peptides listed in Table 2 (SEQ ID NOs: 2-13); or a collection or set of peptides comprising amino acid sequences shifted one residue across the peptide comprising the amino acid sequence DITWEKDAEXTGNSPRLDVA, wherein X is V or I (SEQ ID NO: 1); or (i.e., SEQ ID NOs: 14-22); or a collection or set of peptides comprising amino acid sequences shifted one residue across at least one peptide chosen from the group consisting of the twelve peptides listed in Table 2 (SEQ ID NOs: 2-13); or combinations thereof.

In certain embodiments, the peptides are attached to or immobilized on a solid support. In some embodiments, the peptides are attached to or immobilized on a solid support through a metallic nanolayer (e.g., cadmium, zinc, mercury, gold, silver, copper, or platinum nanolayer). In certain embodiments, the solid support is a bead (e.g., a colloidal particle or a metallic nanoparticle or nanoshell), a flow path in a lateral flow immunoassay device, a flow path in an analytical or centrifugal rotor, a tube or a well (e.g., in a plate), or a sensor (e.g., an electrochemical, optical, or opto-electronic sensor).

Reagents for particular types of assays can also be provided in kits of the invention. Thus, the kits can include a population of beads (e.g., suitable for an agglutination assay or a lateral flow assay), or a plate (e.g., a plate suitable for an ELISA assay). In other embodiments, the kits comprise a device, such as a lateral flow immunoassay device, an analytical or centrifugal rotor, a Western blot, a dot blot, a slot blot, or an electrochemical, optical, or opto-electronic sensor.

In one particular embodiment, the kit would comprise peptide microarrays comprising a peptide or peptides or a collection or set of peptides of the invention, which are reactive with, and specific for ZIKV antibodies, comprising: the peptide comprising the amino acid sequence DITWEKDAEXTGNSPRLDVA, wherein X is V or I (SEQ ID NO: 1); or a peptide chosen from the group consisting of the twelve peptides listed in Table 2 (SEQ ID NOs: 2-13); or a collection or set of peptides comprising amino acid sequences shifted one residue across the peptide comprising the amino acid sequence DITWEKDAEXTGNSPRLDVA, wherein X is V or I (SEQ ID NO: 1) (i.e., SEQ ID NOs: 14-22); or a collection or set of peptides comprising amino acid sequences shifted one residue across at least one peptide chosen from the group consisting of the twelve peptides listed in Table 2 (SEQ ID NOs: 2-13); or combinations thereof.

In addition, the kits can include various diluents and buffers, labeled conjugates or other agents for the detection of specifically bound antigens or antibodies (e.g. labeling reagents), and other signal-generating reagents, such as enzyme substrates, cofactors and chromogens. In some embodiments, the kit comprises an anti-human IgG/IgM antibody conjugated to a detectable label (e.g., a metallic nanoparticle, metallic nanoshell, metallic nanolayer, fluorophore, colored latex particle, or enzyme) as a labeling reagent. In other embodiments, the kit comprises protein A, protein G, protein A/G fusion proteins, protein L, or combinations thereof conjugated to a detectable label (e.g., a metallic nanoparticle, metallic nanoshell, metallic nanolayer, fluorophore, colored latex particle, or enzyme) as a labeling reagent. In still other embodiments, the labeling reagents of the kit are a second collection or set of peptides of the invention conjugated to a detectable label (e.g., a metallic nanoparticle, metallic nanoshell, metallic nanolayer, fluorophore, colored latex particle, or enzyme). The second collection or set of peptides can be the same as or different than the collection or set of peptides, which may optionally be attached to or immobilized upon a solid support.

Other components of a kit can easily be determined by one of skill in the art. Such components may include coating reagents, polyclonal or monoclonal capture antibodies specific for a peptide of the invention, or a cocktail of two or more of the antibodies, purified or semi-purified extracts of these antigens as standards, monoclonal antibody detector antibodies, an anti-mouse, anti-dog, anti-cat, anti-chicken, or anti-human antibody conjugated to a detectable label, indicator charts for colorimetric comparisons, disposable gloves, decontamination instructions, applicator sticks or containers, a sample preparatory cup and buffers or other reagents appropriate for constituting a reaction medium allowing the formation of a peptide-antibody complex.

Such kits provide a convenient, efficient way for a clinical laboratory to diagnose infection by Zika virus. Thus, in certain embodiments, the kits further comprise instructions.

EXAMPLES

The present invention may be better understood by reference to the following non-limiting examples, which are presented in order to more fully illustrate the preferred embodiments of the invention. They should in no way be construed to limit the broad scope of the invention.

Example 1—Generation of 12-Mer Peptides from ZIKV and Additional Viruses 12-mer peptides were selected to represent the whole proteomes of Zika (ZIKV), chikungunya (CHIKV), dengue type 1-4 (DENV 1-4), West Nile (WNV), yellow fever (YFV), and Oropouche (OROV) viruses (Table 1).

TABLE 1

| Selected 12-mer Peptides | | | |
|---|---|---|---|
| | Number of Sequences | Peptides (offset by one) | Unique Peptides |
| ZIKV | 178 | 120,438 | 10,284 |
| CHIKV | 573 | 670,061 | 17,378 |
| DENV (1-4) | 1,161 | 796,173 | 74,108 |
| WNV | 1,438 | 3,620,608 | 34,247 |
| YFV | 218 | 230,915 | 13,440 |
| OROV | 390 | 121,835 | 16,041 |
| | | | 165,498 |

The use of 12-mers reflects three considerations: 1) principal and contextual determinants in antibody recognition of linear epitopes, 2) platform constraints, and 3) preliminary data obtained in experiments with spotted peptide arrays.

Principal and Contextual Determinants in Antibody Recognition of Linear Epitopes:

Serum antibodies bind linear peptide sequences ranging from 5 and 9 amino acids (Buus et al. 2012) and bind most efficiently when targets are flanked by additional amino acids.

Platform Constraints:

The current production version of the platform accommodates up to 3 million 5-18 amino acid peptides. Fidelity of synthesis exceeds 99% for 12-mers; costs increase dramatically and fidelity drops significantly beyond this length.

Preliminary Data.

Experiments performed with spotted 12-mer peptides confirmed that people recently vaccinated against influenza, measles, mumps and rubella had serum antibodies that could be detected by cognate peptides on spotted arrays (Robinson et al. 2002). Therefore a 12 mer peptide can display a single linear epitope recognized by serum antibodies.

The genomic sequences for ZIKV, CHIKV, DENV 1-4, WNV, YFV and OROV were extracted from public databases including GenBank. Coding sequences were used to design suites of 12 amino acid peptides that tile the proteome of individual viruses with an offset of 1 amino acid and an overlap of 11 amino acids.

The Roche NimbleGen (NG) platform used for pyrosequencing and DNA also can be used for the peptide array platform.

The rationale for use of the NG platform for peptides was as follows: 1) NG arrays can be printed in various configurations ranging from 1 to 24 separate arrays per slide; thus, different samples or protocols can be tested simultaneously providing controlled data at a reduced cost; 2) NG arrays are printed on 75 mm×25 mm (3 inch×1 inch) glass slides; this allows use of standard scanners and will facilitate transition to automated clinical applications using robots already in use in pathology and microbiology laboratories; and 3) the NG platform provides the highest feature density in the industry. The printing process has been adapted to allow in situ peptide synthesis. Lasers and focusing mirrors allow photoactivation and precise deposition of either nucleotides or amino acids in a surface area as small as one micron.

The unique peptide sequences (165,498+random control peptides) were printed on Roche-NimbleGen arrays using manufacturer instructions. The arrays were printed with 12 sub-arrays per slide, each with 172,000-feature capacity.

Example 2—Identification of Peptides Specific and Sensitive for ZIKV Antibodies Immune sera were obtained from humans with a history of natural infection with ZIKV, DENV 1-4, and CHIKV from the following three sources: (1) New York City Department of Health and Mental Hygiene: (2) the Ministry of Health of Nicaragua; and (3) Fundação Oswaldo Cruz.

Immune sera was incubated with peptides, washed and then incubated with a fluroresceinated secondary antibody. After scanning for signal the raw data was converted to heat maps that contain corresponding peptide information (i.e. position, sequence).

Figure 1B:
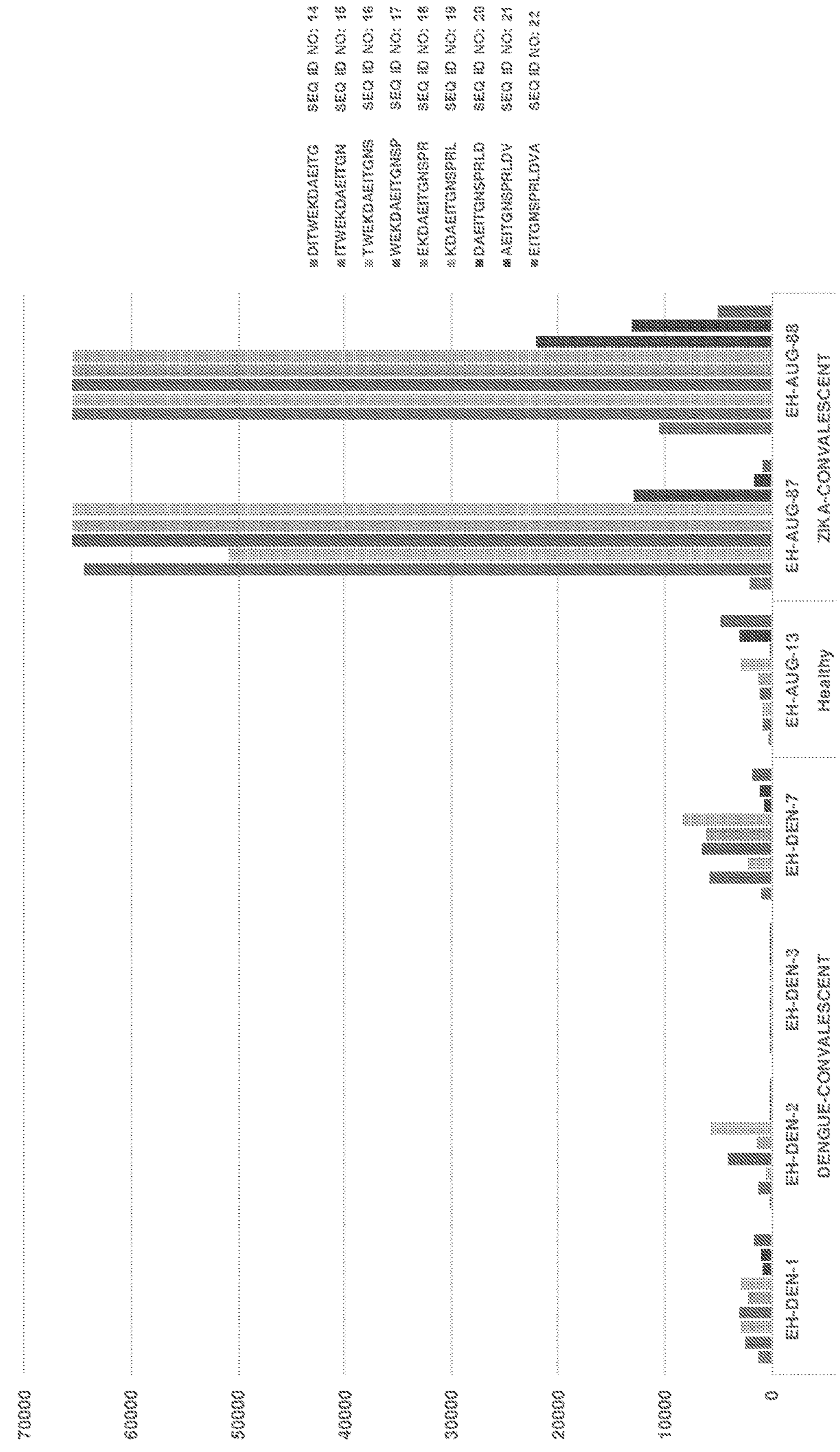
FIG. 1B is a bar diagram showing that the immunoreactive peptide (SEQ ID NO: 1) is specific and discriminatory immunoreactive epitope for Zika virus in NS2B region and that there is no effect of valine to isoleucine mutation in NS2b epitope on reactivity, specificity or discriminatory features. The set of peptides (SEQ ID NOs: 14-22) shifted one residue across the peptide comprising the amino acid sequence DITWEKDAEITGNSPRLDVA (SEQ ID NO: 1) are also specific and discriminatory for the Zika virus. Each bar for each sample represents SEQ ID NOs: 14-22.

FIG. 1A shows seven human sera that were tested on a single Arboviral array. Samples 1-4 were DENV virus positive sera from Nicaragua, sample 5 was from a healthy control, and samples 6 and 7 were ZIKV virus positive sera from Nicaragua. Samples were collected at least 3 weeks after Zika RNA was detected in patients. The peptides with the overlapping and continuous amino acid sequences (SEQ ID NOs: 14-22) of the strong immunoreactive epitope (SEQ ID NO: 1) (426-1434, NS2B-DITWEKDAEVTGNSPRLDVA, Accession ZIKV_AAV34151), are represented by the bars in the graph (one for each peptide, SEQ ID NOs: 14-22, for each sample) and are shown on the right of FIG. 1A.

When the test was done with the peptide with the isoleucine mutation in the NS2b epitope, no effect was found on reactivity, specificity or discriminatory features. Again seven human sera were tested on a single Arboviral array. Samples 1-4 were DENV virus positive sera from Nicaragua, sample 5 was from a healthy control, and samples 6 and 7 were ZIKV virus positive sera from Nicaragua. Samples were collected at least 3 weeks after Zika RNA was detected in patients. The peptides with the overlapping and continuous amino acid sequences (SEQ ID NOs: 14-22) of the strong immunoreactive epitope (SE ID NO: 1) (1430-1438, NS2B-DITWEKDAEITGNSPRLDVA, Accession ZIKV_AMD61711) are represented by the bars in the graph (one for each peptide, SEQ ID NOs: 14-22, for each sample) and are shown on the right of FIG. 1B.

This strongly reactive and specific peptide identified in NS2B region of ZIKV with the amino acid sequence DITWEKDAEXTGNSPRLDVA, wherein X is valine or isoleucine (SEQ ID NO: 1), was reactive in over 90% of Zika convalescent serum samples (FIG. 1).

Twelve other epitopes were identified along the Zika virus proteome with reactivity in over 50% of Zika convalescent serum samples (Table 2).

TABLE 2

Additional Reactive Epitope Peptides of ZIKV

| Identification | Amino acid Sequence |
| --- | --- |
| flavivirus_ZIKV_AF372422_AAK91609; 31-42 | 31-SGMIVNDENRAKVEVTPNSPRAE-42 (SEQ ID NO: 2) |
| flavivirus_ZIKV_AY632535_AAV34151; 447-452 | 447-DEDRAKVEVTPNSPRAE-452 (SEQ ID NO: 3) |
| flavivirus_ZIKV_AY632535_AAV34151; 1499-1501 | 1499-SGALWDVPAPKEVK-1501 (SEQ ID NO: 4) |
| flavivirus_ZIKV_AY632535_AAV34151; 1668-1672 | 1668-REEETPVECFEPSMLK-1672 (SEQ ID NO: 5) |
| flavivirus_ZIKV_AY632535_AAV34151; 1856-1871 | 1856-KTVWFVPSVRNGNEIAACLTKAGKRVI-1871 (SEQ ID NO: 6) |
| flavivirus_ZIKV_AY632535_AAV34151; 1955-1963 | 1955-RGRIGRNPNKPGDEYMYGGG-1963 (SEQ ID NO: 7) |
| flavivirus_ZIKV_AY632535_AAV34151; 2256-2269 | 2256-AVGLLGLITANELGWLERTKNDIAH-2269 (SEQ ID NO: 8) |
| flavivirus_ZIKV_AY632535_AAV34151; 2547-2549 | 2547-GITEVCREEARRAL-2549 (SEQ ID NO: 9) |
| flavivirus_ZIKV_AY632535_AAV34151; 2761-2767 | 2761-DGPRRPVKYEEDVNLGSG-2767 (SEQ ID NO: 10) |
| flavivirus_ZIKV_AY632535_AAV34151; 2923-2940 | 2924-AALGAIFEEEKEWKTAVEAVNDPRFWAL-2940 (SEQ ID NO: 11) |

TABLE 2-continued

| Additional Reactive Epitope Peptides of ZIKV | |
|---|---|
| Identification | Amino acid Sequence |
| flavivirus_ZIKV_AY632535_AAV34151; 3347-3353 | 3347-PVTKWTDIPYLGKREDLW-3353 (SEQ ID NO: 12) |
| flavivirus_ZIKV_AY632535_AAV34151; 2923-2940 | 3368-LIGHRPRTTWAENIKDTVNMVRRIIGD-3383 (SEQ ID NO: 13) |

Example 3—ZIKA NS2B Peptide ELISA

Based on selection of specific peptides with peptide array, which are strongly reactive and specific for ZIKV, a peptide ELISA for the peptide DITWEKDAEVTGNSPRLDVA (SEQ ID NO: 1) was created.

Materials and Methods

Peptide DITWEKDAEVTGNSPRLDVA (SEQ ID NO: 1) was synthesized with biotin or KLH on the N or C terminus, e.g., AGDITWEKDAEVTGNSPRLDVALD{Lys(Biotin/KLH)} (SEQ ID NO: 23). To increase ELISA sensitivity, a 2× concatamer of DITWEKDAEVTGNSPRLDVA (SEQ ID NO: 1) with Biotinylation or KLH on the N or C terminus e.g., contactamer peptide sequence is AGDITWEKDAEVTGNSPRLDVALDEAGDITWEKDAEVTGNSPRLDVALD Lys(Bioti n)/KLH (SEQ ID NO: 24) was also created.

Peptide used for ELISA (underlined amino acids were included as linker or spacer amino acids for ELISA)-

1.ZIKA C TERM LONG P3, (SEQ ID NO: 23)
AGDITWEKDAEVTGNSPRLDVALD{Lys(Biotin)}

2.ZIKA C TERM LONG 2XP3, (SEQ ID NO: 24)
AGDITWEKDAEVTGNSPRLDVALDEAGDITWEKDAEVTGNSPRLDVALD{Lys(Biotin)}

ZIKA NS2B Peptide ELISA Protocol:

Preadsorbed Rabbit Anti-Human IgG H&L (anti-biotin) was coated on 96 well ELISA plate in sealed condition and incubated at 37° C. overnight. Next, plates were washed with PBS-Tween three times, 200 µl/well of blocking solution was added in each well and incubated for 1 hour at RT with lid on. Afterwards plates were washed again with PBS-Tween three times. In next steps, ZIKA C TERM LONG P3 or 2XP3 were diluted in blocking solution and 100 ul/well were added and incubated at 37° C. for 90 minutes with lid on. Plates were washed 3 times with PBS-Tween. Primary antibody (serum, plasma, CSF or urine) were diluted in blocking solution and 200 µL/well added and, if appropriate, serially diluted. The plate containing the diluted specimen and coated with anti-biotin capture antibody and the bound Zika peptide was incubated for 90 minutes at 37° C. After 3 times washing with PBS-Tween, Goat Anti-Human IgG HRP conjugate was used at 1:5000 dilution (100 µL/well) and incubated for 90 minutes at 37° C., followed by washing 3 times with PBS-Tween. Finally, chromogenic substrate (Ultra TMB) and stop solution were added and plates were read on a plate reader at 450 nm.

Sera from humans with a history of natural infection with ZIKV, DENV 1-4 and CHIKV through collaborators from Nicaragua, Brazil, Puerto Rico, the National Institutes of Health and New York City Department of Health and Mental Hygiene (NYCDOHMH) (returning travelers) was used in the assay.

Results

Screening of peptide arrays enabled discovery of a specific peptide sequence in NS2b of ZIKA (DITWEKDAEVTGNSPRLDVA (SEQ ID NO: 1) that had greater than 80% sensitivity with sera from individuals with documented ZIKV infection. Bioinformatic analysis confirmed that this peptide has no significant homology to NS2b of dengue viruses. Its utility was confirmed in an ELISA based on synthesis of soluble peptides biotinyated at the amino- or carboxy-terminus to facilitate attachment to the matrix vis a capture antibody. Optimization enabled design of a Zika NS2b-peptide ELISA with 95.3% sensitivity and 94.5% specificity for ZIKV.

Figure 2:
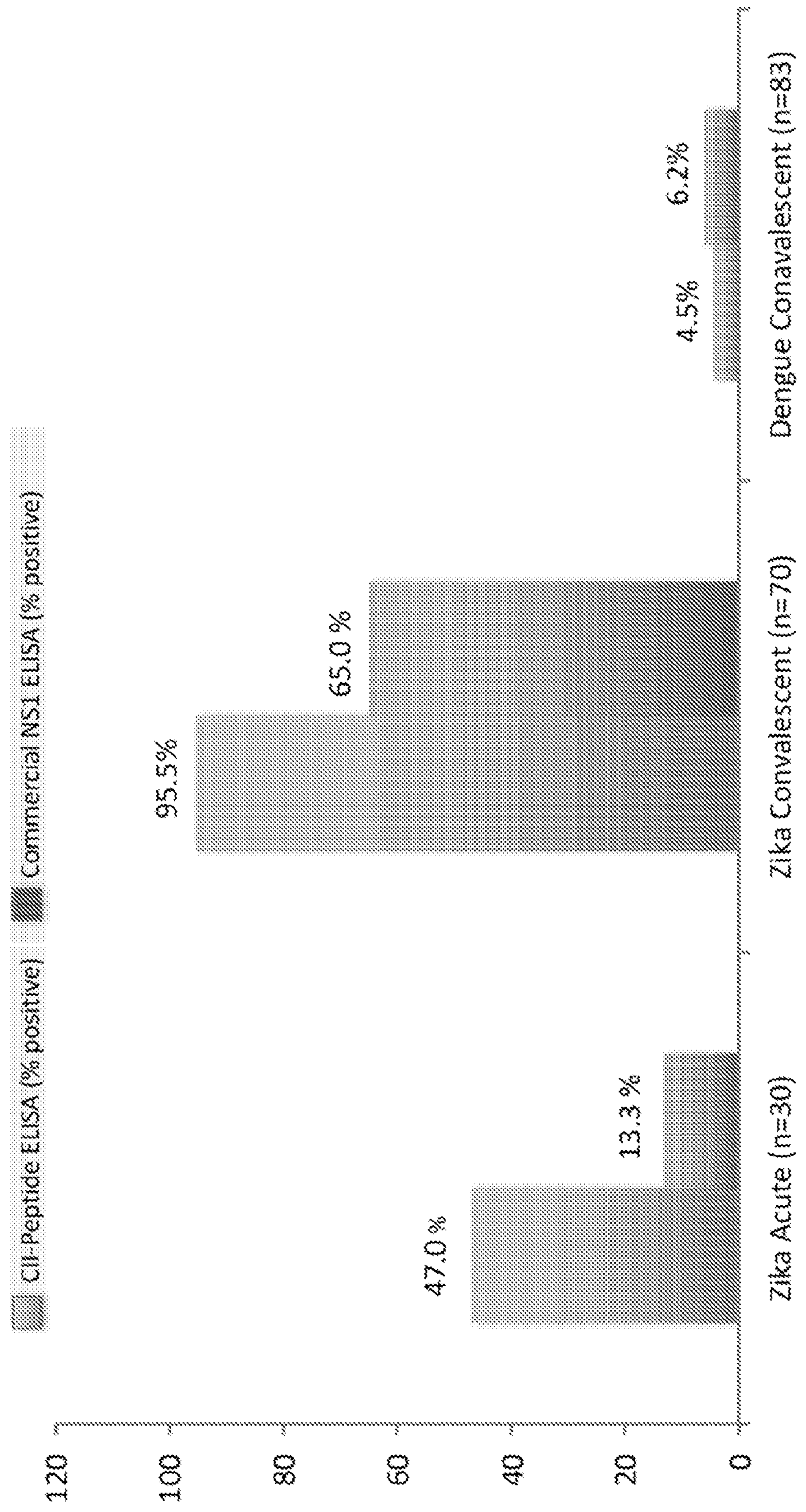
FIG. 2 is a graph showing the results of the comparison of a commercial ELISA assay with an ELISA assay using a peptide of the invention (SEQ ID NO: 1). The graph shows the percent of known Zika-positive sera detected by the commercial ELISA (right hand bars) and the ELISA assay using a peptide of the invention (SEQ ID NO: 1) (left hand bars).

Additionally, the performance of the NS2b-peptide ELISA and a commercial ELISA (Euroimmun) was compared with acute and convalescent sera from Zika patients. With both sera, the NS2b-peptide ELISA had a higher sensitivity than the commercial NS1 ELISA (FIG. 2).

REFERENCES

Anderson et al. *J. Immunol. Methods* 2011; 366:79-88.
Broutet et al. *N. Engl. J. Med.* 2016 Apr. 21; 374(16):1506-9.
Buus et al. *Mol. Cell Proteomics* 2012; 11:1790-800.
Rasmussen et al. *N. Engl. J. Med.* 2016 May 19; 374(20):1981-7.
Robinson et al. *Nat. Med.* 2002; 8:295-301.
Vigil et al. *Future Microbiol.* 2010; 5:241-51. PMC2841399

The invention claimed is:

1. A method for the serological detection of an antibody to Zika virus in a sample, comprising:

a. contacting the sample with a collection of isolated non-redundant peptides specific for antibodies to Zika virus, wherein the peptides are 5 amino acids to 20 amino acids in length of the sequences set forth in SEQ ID NO: 1 or SEQ ID NOS:14-22, under conditions sufficient to allow the binding of the antibody(ies) to the peptide(s);

b. washing antibodies that have not bound to the isolated non-redundant peptides;

c. labeling bound antibodies with a detectable label; and d. detecting formation of an antibody-peptide complex comprising said one or more peptides in the collection, wherein formation of the complex is indicative of an antibody to an epitope of a Zika antigen being present in the sample.

2. The method of claim 1, wherein the sample is from a subject.

3. The method of claim 2, wherein the subject is a human female.

4. The method of claim 3, wherein the subject is pregnant.

5. The method of claim 2, wherein the subject is a test subject which has been administered a Zika virus vaccine or immunomodulatory agent.

6. The method of claim 2, wherein the subject had a seropositive result on an enzyme-linked immunosorbent assay (ELISA).

7. The method of claim 1, wherein the sample is chosen from the group consisting of nasopharyngeal aspirate, blood, cerebrospinal fluid, saliva, serum, plasma, urine, sputum, bronchial lavage, pericardial fluid, and peritoneal fluid.

8. The method of claim 1, wherein the collection of peptides is immobilized to a solid support.

9. The method of claim 1, wherein the detecting step comprises performing an ELISA assay.

10. The method of claim 1, wherein the collection of peptides comprises peptides which are 12 amino acids in length.

11. The method of claim 1, wherein the collection of peptides comprises peptides of SEQ ID NOs: 14-22.

12. A method for the serological detection of an antibody to Zika virus in a sample, comprising:

a. contacting the sample with a collection of isolated non-redundant peptides specific for antibodies to Zika virus, wherein the peptides are 5 amino acids to 20 amino acids in length of the sequences set forth in SEQ ID NOs: 2-13 and over 50% reactive in Zika virus convalescent serum samples, under conditions sufficient to allow the binding of the antibody(ies) to the peptide(s);

b. washing antibodies that have not bound to the isolated non-redundant peptides;

c. labeling bound antibodies with a detectable label; and d. detecting formation of an antibody-peptide complex comprising said one or more peptides in the collection, wherein formation of the complex is indicative of an antibody to an epitope of a Zika antigen being present in the sample.

13. The method of claim 12, wherein the collection of peptides comprises peptides 12 amino acids in length.

14. The method of claim 12, wherein the sample is from a subject.

15. The method of claim 12, wherein the subject is a human female.

16. The method of claim 12, wherein the subject is pregnant.

17. The method of claim 12, wherein the subject is a test subject which has been administered a Zika virus vaccine or immunomodulatory agent.

18. The method of claim 12, wherein the sample is chosen from the group consisting of nasopharyngeal aspirate, blood, cerebrospinal fluid, saliva, serum, plasma, urine, sputum, bronchial lavage, pericardial fluid, and peritoneal fluid.

19. The method of claim 12, wherein the collection of peptides is immobilized to a solid support.

20. The method of claim 12, wherein the detecting step comprises performing an ELISA assay.

* * * * *

SEQUENCE LISTING

```
<160> NUMBER OF SEQ ID NOS: 24

<210> SEQ ID NO 1
<211> LENGTH: 20
<212> TYPE: PRT
<213> ORGANISM: Artificial Sequence
<220> FEATURE:
<223> OTHER INFORMATION: Zika antigenic peptide
```

-continued

<220> FEATURE:
<221> NAME/KEY: misc_feature
<222> LOCATION: (10)..(10)
<223> OTHER INFORMATION: X can be valine or isoleucine

<400> SEQUENCE: 1

```
Asp Ile Thr Trp Glu Lys Asp Ala Glu Xaa Thr Gly Asn Ser Pro Arg
1               5                   10                  15

Leu Asp Val Ala
            20
```

<210> SEQ ID NO 2
<211> LENGTH: 23
<212> TYPE: PRT
<213> ORGANISM: Artificial sequence
<220> FEATURE:
<223> OTHER INFORMATION: Zika antigenic peptide

<400> SEQUENCE: 2

```
Ser Gly Met Ile Val Asn Asp Glu Asn Arg Ala Lys Val Glu Val Thr
1               5                   10                  15

Pro Asn Ser Pro Arg Ala Glu
            20
```

<210> SEQ ID NO 3
<211> LENGTH: 17
<212> TYPE: PRT
<213> ORGANISM: Artificial sequence
<220> FEATURE:
<223> OTHER INFORMATION: Zika antigenic peptide

<400> SEQUENCE: 3

```
Asp Glu Asp Arg Ala Lys Val Glu Val Thr Pro Asn Ser Pro Arg Ala
1               5                   10                  15

Glu
```

<210> SEQ ID NO 4
<211> LENGTH: 14
<212> TYPE: PRT
<213> ORGANISM: Artificial sequence
<220> FEATURE:
<223> OTHER INFORMATION: Zika antigenic peptide

<400> SEQUENCE: 4

```
Ser Gly Ala Leu Trp Asp Val Pro Ala Pro Lys Glu Val Lys
1               5                   10
```

<210> SEQ ID NO 5
<211> LENGTH: 16
<212> TYPE: PRT
<213> ORGANISM: Artificial sequence
<220> FEATURE:
<223> OTHER INFORMATION: Zika antigenic peptide

<400> SEQUENCE: 5

```
Arg Glu Glu Glu Thr Pro Val Glu Cys Phe Glu Pro Ser Met Leu Lys
1               5                   10                  15
```

<210> SEQ ID NO 6
<211> LENGTH: 27
<212> TYPE: PRT
<213> ORGANISM: Artificial sequence
<220> FEATURE:
<223> OTHER INFORMATION: Zika antigenic peptide

<400> SEQUENCE: 6

```
Lys Thr Val Trp Phe Val Pro Ser Val Arg Asn Gly Asn Glu Ile Ala
1               5                   10                  15

Ala Cys Leu Thr Lys Ala Gly Lys Arg Val Ile
            20                  25


<210> SEQ ID NO 7
<211> LENGTH: 20
<212> TYPE: PRT
<213> ORGANISM: Artificial sequence
<220> FEATURE:
<223> OTHER INFORMATION: Zika antigenic peptide

<400> SEQUENCE: 7

Arg Gly Arg Ile Gly Arg Asn Pro Asn Lys Pro Gly Asp Glu Tyr Met
1               5                   10                  15

Tyr Gly Gly Gly
            20


<210> SEQ ID NO 8
<211> LENGTH: 25
<212> TYPE: PRT
<213> ORGANISM: Artificial sequence
<220> FEATURE:
<223> OTHER INFORMATION: Zika antigenic peptide

<400> SEQUENCE: 8

Ala Val Gly Leu Leu Gly Leu Ile Thr Ala Asn Glu Leu Gly Trp Leu
1               5                   10                  15

Glu Arg Thr Lys Asn Asp Ile Ala His
            20                  25


<210> SEQ ID NO 9
<211> LENGTH: 14
<212> TYPE: PRT
<213> ORGANISM: Artificial sequence
<220> FEATURE:
<223> OTHER INFORMATION: Zika antigenic peptide

<400> SEQUENCE: 9

Gly Ile Thr Glu Val Cys Arg Glu Glu Ala Arg Arg Ala Leu
1               5                   10


<210> SEQ ID NO 10
<211> LENGTH: 18
<212> TYPE: PRT
<213> ORGANISM: Artificial sequence
<220> FEATURE:
<223> OTHER INFORMATION: Zika antigenic peptide

<400> SEQUENCE: 10

Asp Gly Pro Arg Arg Pro Val Lys Tyr Glu Glu Asp Val Asn Leu Gly
1               5                   10                  15

Ser Gly


<210> SEQ ID NO 11
<211> LENGTH: 28
<212> TYPE: PRT
<213> ORGANISM: Artificial sequence
<220> FEATURE:
<223> OTHER INFORMATION: Zika antigenic peptide

<400> SEQUENCE: 11

Ala Ala Leu Gly Ala Ile Phe Glu Glu Glu Lys Glu Trp Lys Thr Ala
1               5                   10                  15
```

Val Glu Ala Val Asn Asp Pro Arg Phe Trp Ala Leu
20 25

<210> SEQ ID NO 12
<211> LENGTH: 18
<212> TYPE: PRT
<213> ORGANISM: Artificial sequence
<220> FEATURE:
<223> OTHER INFORMATION: Zika antigenic peptide

<400> SEQUENCE: 12

Pro Val Thr Lys Trp Thr Asp Ile Pro Tyr Leu Gly Lys Arg Glu Asp
1 5 10 15

Leu Trp

<210> SEQ ID NO 13
<211> LENGTH: 27
<212> TYPE: PRT
<213> ORGANISM: Artificial sequence
<220> FEATURE:
<223> OTHER INFORMATION: Zika antigenic peptide

<400> SEQUENCE: 13

Leu Ile Gly His Arg Pro Arg Thr Thr Trp Ala Glu Asn Ile Lys Asp
1 5 10 15

Thr Val Asn Met Val Arg Arg Ile Ile Gly Asp
20 25

<210> SEQ ID NO 14
<211> LENGTH: 12
<212> TYPE: PRT
<213> ORGANISM: Artificial sequence
<220> FEATURE:
<223> OTHER INFORMATION: Zika antigenic peptide
<220> FEATURE:
<221> NAME/KEY: misc_feature
<222> LOCATION: (10)..(10)
<223> OTHER INFORMATION: X can be valine or isoleucine

<400> SEQUENCE: 14

Asp Ile Thr Trp Glu Lys Asp Ala Glu Xaa Thr Gly
1 5 10

<210> SEQ ID NO 15
<211> LENGTH: 12
<212> TYPE: PRT
<213> ORGANISM: Artificial sequence
<220> FEATURE:
<223> OTHER INFORMATION: Zika antigenic peptide
<220> FEATURE:
<221> NAME/KEY: misc_feature
<222> LOCATION: (9)..(9)
<223> OTHER INFORMATION: X can be valine or isoleucine

<400> SEQUENCE: 15

Ile Thr Trp Glu Lys Asp Ala Glu Xaa Thr Gly Asn
1 5 10

<210> SEQ ID NO 16
<211> LENGTH: 12
<212> TYPE: PRT
<213> ORGANISM: Artificial sequence
<220> FEATURE:
<223> OTHER INFORMATION: Zika antigenic peptide
<220> FEATURE:
<221> NAME/KEY: misc_feature
<222> LOCATION: (8)..(8)

<223> OTHER INFORMATION: X can be valine or isoleucine

<400> SEQUENCE: 16

Thr Trp Glu Lys Asp Ala Glu Xaa Thr Gly Asn Ser
1               5                   10

<210> SEQ ID NO 17
<211> LENGTH: 12
<212> TYPE: PRT
<213> ORGANISM: Artificial sequence
<220> FEATURE:
<223> OTHER INFORMATION: Zika antigenic peptide
<220> FEATURE:
<221> NAME/KEY: misc_feature
<222> LOCATION: (7)..(7)
<223> OTHER INFORMATION: X can be valine or isoleucine

<400> SEQUENCE: 17

Trp Glu Lys Asp Ala Glu Xaa Thr Gly Asn Ser Pro
1               5                   10

<210> SEQ ID NO 18
<211> LENGTH: 12
<212> TYPE: PRT
<213> ORGANISM: Artificial sequence
<220> FEATURE:
<223> OTHER INFORMATION: Zika antigenic peptide
<220> FEATURE:
<221> NAME/KEY: misc_feature
<222> LOCATION: (6)..(6)
<223> OTHER INFORMATION: X can be valine or isoleucine

<400> SEQUENCE: 18

Glu Lys Asp Ala Glu Xaa Thr Gly Asn Ser Pro Arg
1               5                   10

<210> SEQ ID NO 19
<211> LENGTH: 12
<212> TYPE: PRT
<213> ORGANISM: Artificial sequence
<220> FEATURE:
<223> OTHER INFORMATION: Zika antigenic peptide
<220> FEATURE:
<221> NAME/KEY: misc_feature
<222> LOCATION: (5)..(5)
<223> OTHER INFORMATION: X can be valine or isoleucine

<400> SEQUENCE: 19

Lys Asp Ala Glu Xaa Thr Gly Asn Ser Pro Arg Leu
1               5                   10

<210> SEQ ID NO 20
<211> LENGTH: 12
<212> TYPE: PRT
<213> ORGANISM: Artificial sequence
<220> FEATURE:
<223> OTHER INFORMATION: Zika antigenic peptide
<220> FEATURE:
<221> NAME/KEY: misc_feature
<222> LOCATION: (4)..(4)
<223> OTHER INFORMATION: X can be valine or isoleucine

<400> SEQUENCE: 20

Asp Ala Glu Xaa Thr Gly Asn Ser Pro Arg Leu Asp
1               5                   10

<210> SEQ ID NO 21
<211> LENGTH: 12
<212> TYPE: PRT

<213> ORGANISM: Artificial sequence
<220> FEATURE:
<223> OTHER INFORMATION: Zika antigenic peptide
<220> FEATURE:
<221> NAME/KEY: misc_feature
<222> LOCATION: (3)..(3)
<223> OTHER INFORMATION: X can be valine or isoleucine

<400> SEQUENCE: 21

Ala Glu Xaa Thr Gly Asn Ser Pro Arg Leu Asp Val
1               5                   10

<210> SEQ ID NO 22
<211> LENGTH: 12
<212> TYPE: PRT
<213> ORGANISM: Artificial sequence
<220> FEATURE:
<223> OTHER INFORMATION: Zika antigenic peptide
<220> FEATURE:
<221> NAME/KEY: misc_feature
<222> LOCATION: (2)..(2)
<223> OTHER INFORMATION: X can be valine or isoleucine

<400> SEQUENCE: 22

Glu Xaa Thr Gly Asn Ser Pro Arg Leu Asp Val Ala
1               5                   10

<210> SEQ ID NO 23
<211> LENGTH: 24
<212> TYPE: PRT
<213> ORGANISM: Artificial sequence
<220> FEATURE:
<223> OTHER INFORMATION: Zika antigenic peptide
<220> FEATURE:
<221> NAME/KEY: misc_feature
<222> LOCATION: (12)..(12)
<223> OTHER INFORMATION: X can be valine or isoleucine

<400> SEQUENCE: 23

Ala Gly Asp Ile Thr Trp Glu Lys Asp Ala Glu Xaa Thr Gly Asn Ser
1               5                   10                  15

Pro Arg Leu Asp Val Ala Leu Asp
            20

<210> SEQ ID NO 24
<211> LENGTH: 49
<212> TYPE: PRT
<213> ORGANISM: Artificial sequence
<220> FEATURE:
<223> OTHER INFORMATION: Zika antigenic peptide
<220> FEATURE:
<221> NAME/KEY: misc_feature
<222> LOCATION: (12)..(12)
<223> OTHER INFORMATION: X can be valine or isoleucine
<220> FEATURE:
<221> NAME/KEY: misc_feature
<222> LOCATION: (37)..(37)
<223> OTHER INFORMATION: X can be valine or isoleucine

<400> SEQUENCE: 24

Ala Gly Asp Ile Thr Trp Glu Lys Asp Ala Glu Xaa Thr Gly Asn Ser
1               5                   10                  15

Pro Arg Leu Asp Val Ala Leu Asp Glu Ala Gly Asp Ile Thr Trp Glu
            20                  25                  30

Lys Asp Ala Glu Xaa Thr Gly Asn Ser Pro Arg Leu Asp Val Ala Leu
        35                  40                  45

Asp